(12) United States Patent
Long

(10) Patent No.: US 7,097,644 B2
(45) Date of Patent: Aug. 29, 2006

(54) MEDICAL DEVICE WITH IMPROVED WALL CONSTRUCTION

(75) Inventor: Gary L. Long, Gerards Cross (GB)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 10/394,285

(22) Filed: Mar. 21, 2003

(65) Prior Publication Data

US 2003/0216727 A1    Nov. 20, 2003

Related U.S. Application Data

(63) Continuation-in-part of application No. 10/245,928, filed on Sep. 18, 2002, which is a continuation-in-part of application No. 10/105,722, filed on Mar. 25, 2002, now Pat. No. 6,918,906.

(60) Provisional application No. 60/280,009, filed on Mar. 30, 2001.

(51) Int. Cl.
*A61B 18/14* (2006.01)

(52) U.S. Cl. .......................... 606/41; 606/49
(58) Field of Classification Search .............. 60/41–49, 60/129, 176, 183
See application file for complete search history.

(56) References Cited

U.S. PATENT DOCUMENTS

| | | | |
|---|---|---|---|
| 874,810 A | 12/1907 | Wappler | |
| 1,624,716 A | 4/1927 | Cerbo | |
| 3,939,839 A | 2/1976 | Curtiss | |
| 4,202,336 A | * 5/1980 | van Gerven | 606/21 |
| 4,237,871 A | 12/1980 | Bonnet | |
| 4,532,924 A | 8/1985 | Auth et al. | |
| 4,582,057 A | 4/1986 | Auth et al. | |
| 4,646,722 A | 3/1987 | Silverstein et al. | |
| 4,682,596 A | 7/1987 | Bales et al. | |
| 4,729,384 A | 3/1988 | Bazenet et al. | |
| 4,765,331 A | 8/1988 | Petruzzi et al. | |
| 4,807,593 A | 2/1989 | Ito | |
| 4,819,620 A | 4/1989 | Okutsu | |
| 5,025,778 A | 6/1991 | Silverstein et al. | |
| 5,080,660 A | 1/1992 | Buelna | |
| 5,112,308 A | 5/1992 | Olsen et al. | |
| 5,122,138 A | 6/1992 | Manwaring | |
| 5,156,151 A | 10/1992 | Imran | |
| 5,336,222 A | 8/1994 | Durgin, Jr. et al. | |
| 5,354,302 A | 10/1994 | Ko | |
| 5,395,327 A | * 3/1995 | Lundquist et al. | 604/528 |
| 5,500,012 A | 3/1996 | Brucker et al. | |
| 5,507,725 A | * 4/1996 | Savage et al. | 604/95.04 |
| 5,681,282 A | 10/1997 | Eggers et al. | |
| 5,695,448 A | 12/1997 | Kimura et al. | |

(Continued)

FOREIGN PATENT DOCUMENTS

JP      01/079017      10/1999

(Continued)

OTHER PUBLICATIONS

PCT International Search Report dated Apr. 4, 2003 for international application No. PCT/US02/10185.

(Continued)

*Primary Examiner*—Roy D. Gibson
*Assistant Examiner*—Aaron Roane
(74) *Attorney, Agent, or Firm*—Victor Moreno

(57) ABSTRACT

A medical device having a laminate elongate hollow member is disclosed. The laminate member provides torsional stiffness for controlling positioning of the distal end of the device, and provides bending flexibility for assisting in insertion of the device in the patient's esophagus or other body lumen.

5 Claims, 23 Drawing Sheets

U.S. PATENT DOCUMENTS

| | | | |
|---|---|---|---|
| 5,697,882 | A | 12/1997 | Eggers et al. |
| 5,697,909 | A | 12/1997 | Eggers et al. |
| 5,746,696 | A | 5/1998 | Kondo |
| 5,749,899 | A | 5/1998 | Bardin |
| 5,766,152 | A | 6/1998 | Morley et al. |
| 5,766,153 | A | 6/1998 | Eggers et al. |
| 5,782,760 | A | 7/1998 | Schaer |
| 5,782,824 | A | 7/1998 | Abela et al. |
| 5,789,047 | A | 8/1998 | Sasaki et al. |
| 5,846,182 | A | 12/1998 | Wolcott |
| 5,861,002 | A | 1/1999 | Desai |
| 5,873,877 | A | 2/1999 | McGaffigan et al. |
| 5,888,198 | A | 3/1999 | Eggers et al. |
| 5,902,272 | A | 5/1999 | Eggers et al. |
| 5,941,834 | A | 8/1999 | Skladnev |
| 5,961,526 | A | 10/1999 | Chu et al. |
| 5,986,693 | A | 11/1999 | Adair et al. |
| 6,009,877 | A | 1/2000 | Edwards |
| 6,010,450 | A | 1/2000 | Perkins |
| 6,022,334 | A | 2/2000 | Edwards et al. |
| 6,027,499 | A | 2/2000 | Johnston |
| 6,056,744 | A | 5/2000 | Edwards |
| 6,066,134 | A | 5/2000 | Eggers et al. |
| 6,068,603 | A | 5/2000 | Suzuki |
| 6,071,233 | A * | 6/2000 | Ishikawa et al. ............ 600/104 |
| 6,086,583 | A | 7/2000 | Ouchi |
| 6,091,993 | A | 7/2000 | Bouchier et al. |
| 6,091,995 | A | 7/2000 | Ingle et al. |
| 6,102,434 | A | 8/2000 | Ohlert et al. |
| 6,106,521 | A | 8/2000 | Blewett et al. |
| 6,120,434 | A | 9/2000 | Kimura et al. |
| 6,142,931 | A | 11/2000 | Kaji |
| 6,146,378 | A | 11/2000 | Mikus et al. |
| 6,149,620 | A | 11/2000 | Baker et al. |
| 6,178,354 | B1 | 1/2001 | Gibson |
| 6,179,832 | B1 | 1/2001 | Jones et al. |
| 6,190,381 | B1 | 2/2001 | Olsen et al. |
| 6,235,020 | B1 | 5/2001 | Cheng et al. |
| 6,238,389 | B1 | 5/2001 | Paddock et al. |
| 6,241,140 | B1 | 6/2001 | Adams et al. |
| 6,241,702 | B1 | 6/2001 | Lundquist et al. |
| 6,241,724 | B1 | 6/2001 | Fleischman et al. |
| 6,254,598 | B1 | 7/2001 | Edwards et al. |
| 6,258,087 | B1 | 7/2001 | Edwards et al. |
| 6,296,638 | B1 | 10/2001 | Davison et al. |
| 6,309,379 | B1 | 10/2001 | Willard et al. |
| 6,325,798 | B1 | 12/2001 | Edwards et al. |
| 6,355,034 | B1 | 3/2002 | Cosmescu |
| 6,358,197 | B1 | 3/2002 | Silverman et al. |
| 6,394,949 | B1 * | 5/2002 | Crowley et al. ............ 600/127 |
| 6,402,742 | B1 | 6/2002 | Blewett et al. |
| 6,405,732 | B1 | 6/2002 | Edwards et al. |
| 6,551,310 | B1 | 4/2003 | Ganz et al. |
| 6,556,673 | B1 | 4/2003 | Davis |
| 6,645,201 | B1 | 11/2003 | Utley et al. |
| 6,689,130 | B1 | 2/2004 | Arai et al. |
| 6,740,082 | B1 | 5/2004 | Shadduck |
| 6,813,520 | B1 | 11/2004 | Sampson et al. |
| 6,869,395 | B1 | 3/2005 | Page et al. |
| 2002/0147447 | A1 | 10/2002 | Long |
| 2002/0156470 | A1 | 10/2002 | Shadduck |
| 2002/0177847 | A1 | 11/2002 | Long |
| 2002/0183739 | A1 | 12/2002 | Long |
| 2003/0009162 | A1 | 1/2003 | Messing et al. |
| 2003/0009163 | A1 | 1/2003 | Messing et al. |
| 2003/0181905 | A1 | 9/2003 | Long |
| 2003/0216727 | A1 | 11/2003 | Long |

FOREIGN PATENT DOCUMENTS

| | | |
|---|---|---|
| WO | 01/35846 A1 | 5/1991 |
| WO | WO01/24721 | 8/1998 |
| WO | WO 99/00060 A | 1/1999 |
| WO | 99/35986 A1 | 7/1999 |
| WO | 00/18314 A1 | 4/2000 |
| WO | 00/19926 A1 | 4/2000 |
| WO | WO 00/19926 A | 4/2000 |
| WO | 00/35364 A1 | 6/2000 |
| WO | WO 00/32130 A | 6/2000 |
| WO | WO 01/12012 A | 2/2001 |
| WO | WO 02/47569 A | 6/2002 |
| WO | WO 02/078557 A1 | 10/2002 |

OTHER PUBLICATIONS

PCT Written Opinion regarding PCT/US02/10185.
Guiterrez, Jorge G. et al., A Multipurpose Overtube for Diagnostic and Therapeutic Flexible Fiberoptic Endoscopy. *Gastrointestinal Endoscopy*, 1986, 32(4):274-277.
Rogers, B.H. Gerald et al, An Overtube for the Flexible Fiberoptic Esophagogastroduodenscope. *Gastrointestinal Endoscopy*, 1982, 28(4): 256-57.
EPO Search Report dated Jan. 5, 2004 for related U.S. Appl. No. 10/245,928, European Patent Application No. 03/255838.9.
U.S. Appl. No. 10/105,722, filed Mar. 25, 2002, Gary L. Long.
U.S. Appl. No. 10/105,610, filed Mar. 25, 2002, Gary L. Long.
U.S. Appl. No. 10/105,609, filed Mar. 25, 2002, Gary L. Long.
U.S. Appl. No. 10/245,028, filed Sep. 18, 2002, Gary L. Long.
U.S. Appl. No. 10/246,056, filed Sep. 18, 2002, Gary L. Long.
EP Supplementary Search Report dated Oct. 25, 2005, for corresponding application EP 02 757924.
EP Supplementary Search Report dated Dec. 5, 2005, for related application EP 02 723726.
EPO Search Report dated, Jul. 26, 2004 for related European Patent Application No. EP 04 25 1414.
PCT International Search Report PCT/US02/09975 dated Mar. 27, 2003, which corresponds to related U.S. Appl. No. 10/105,609.
EPO Communication dated Mar. 16, 2006 for corresponding patent application 02 723 726.2.

* cited by examiner

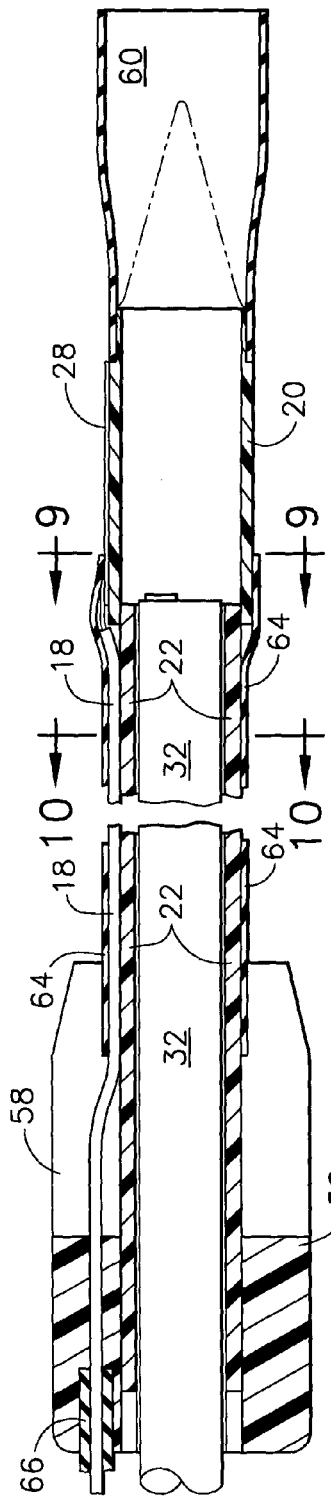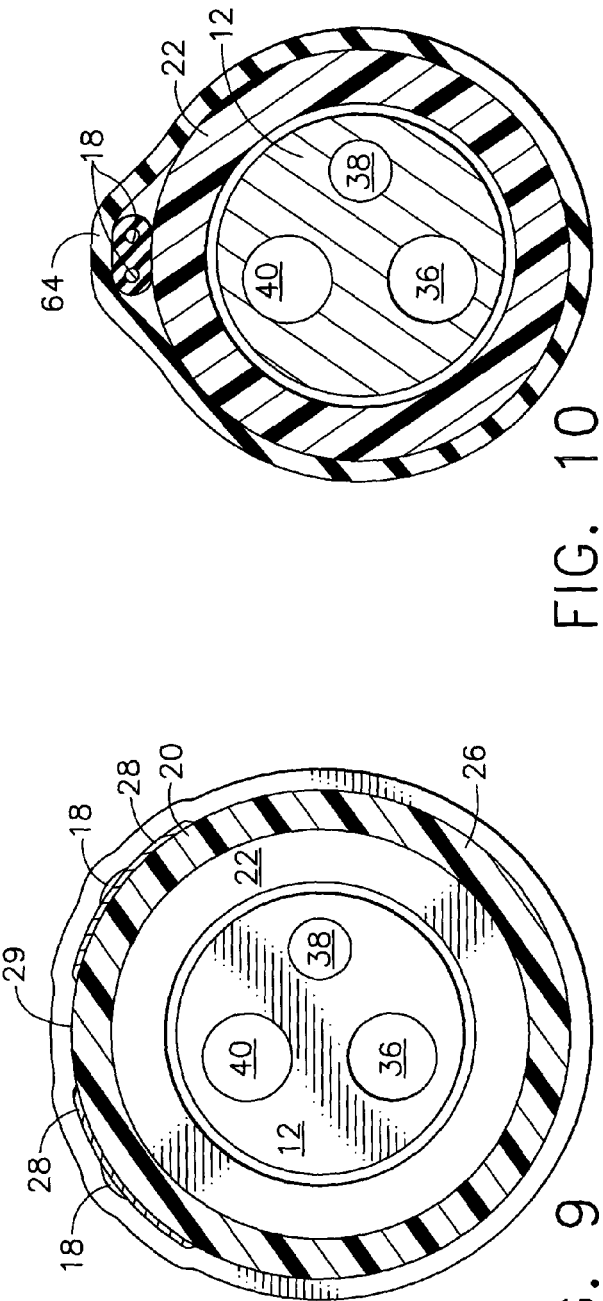

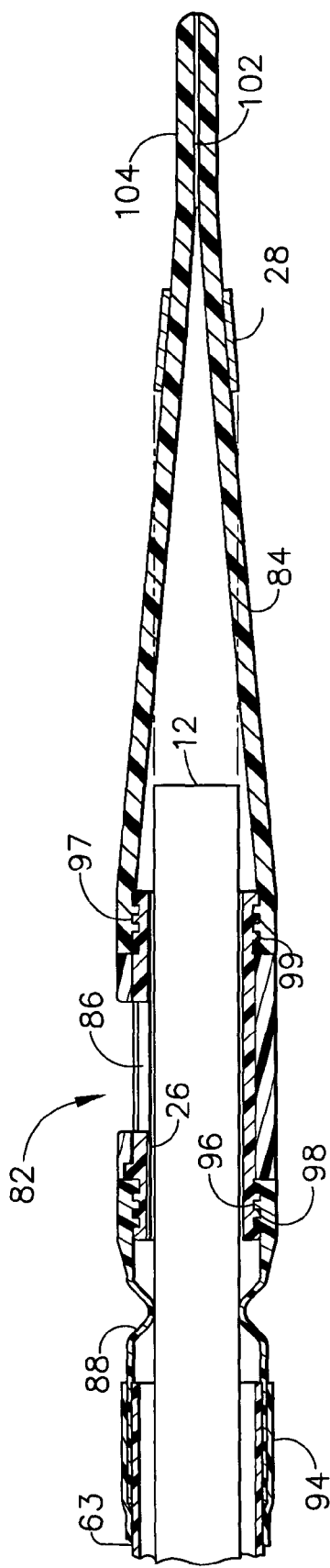
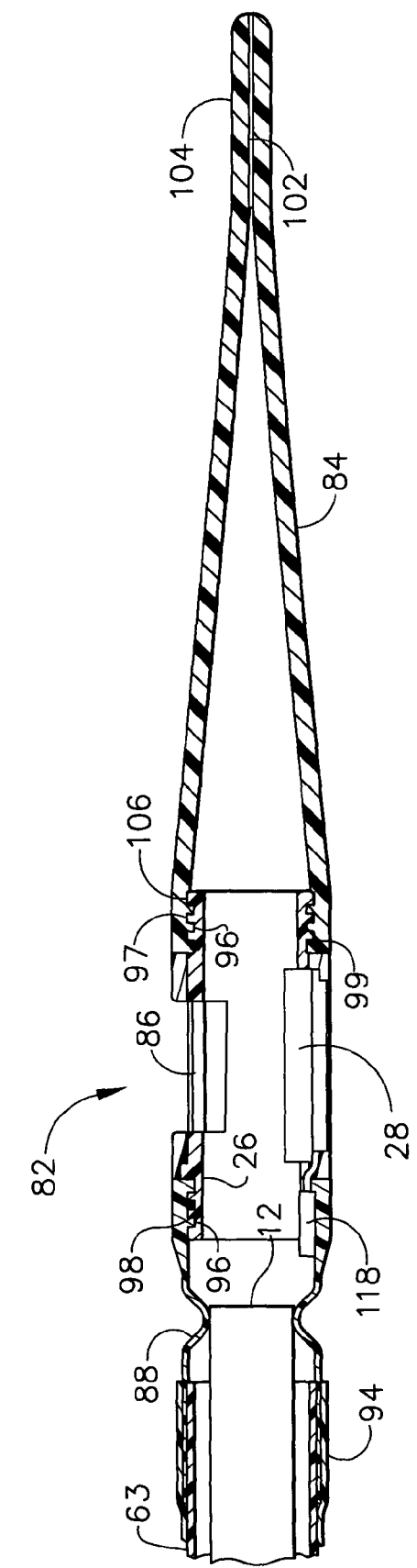
FIG. 18
FIG. 19

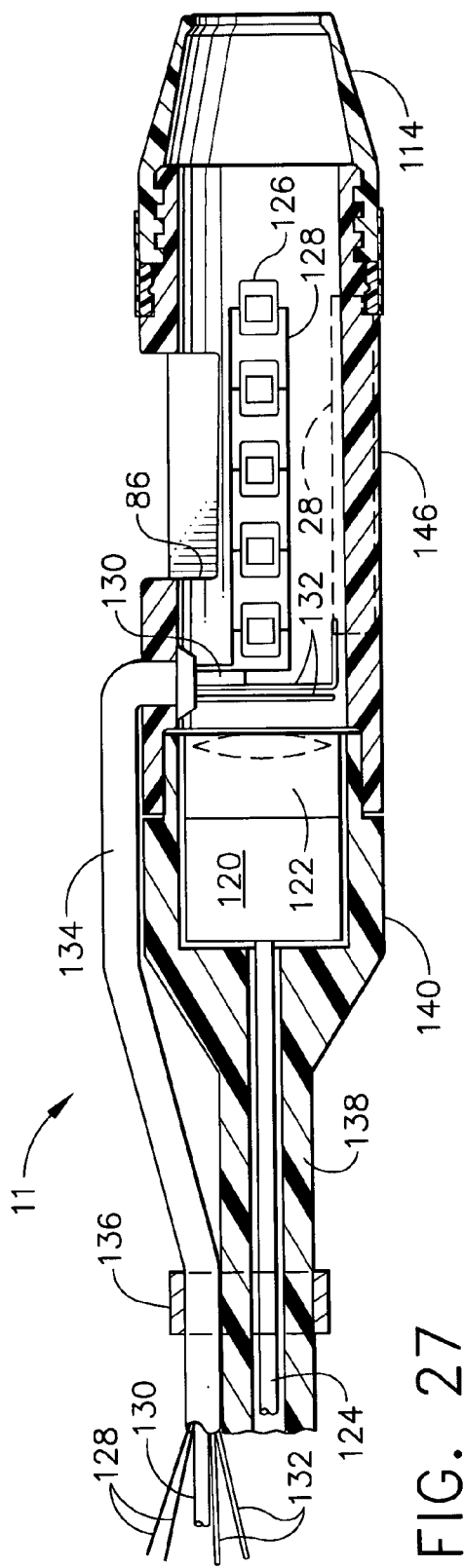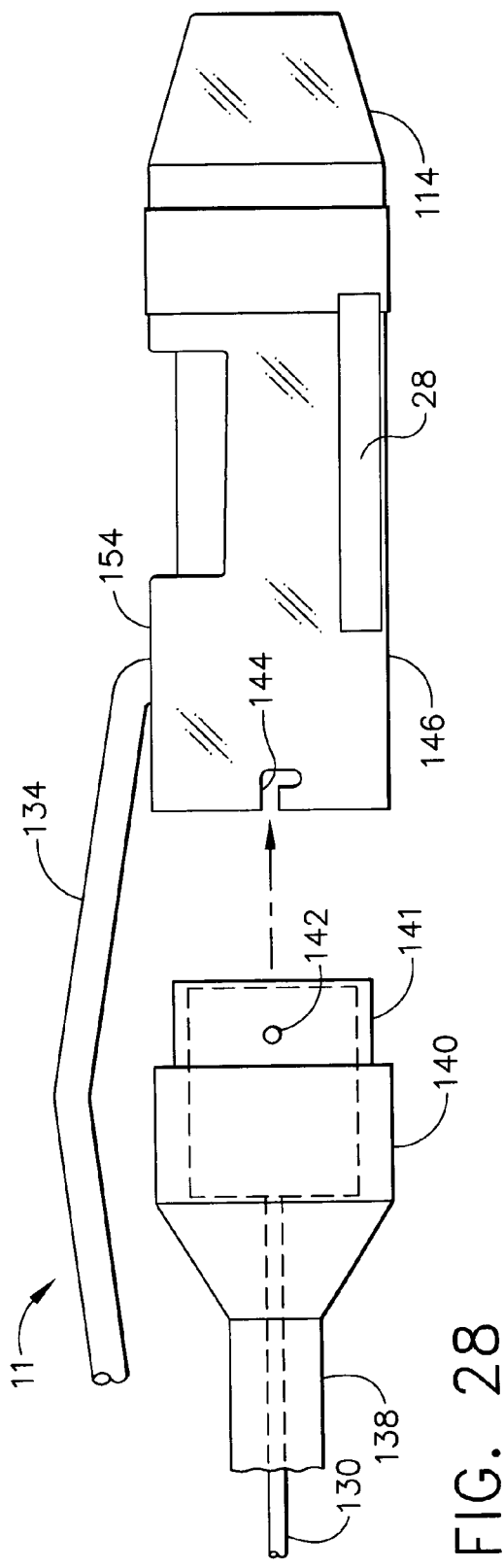

MEDICAL DEVICE WITH IMPROVED WALL CONSTRUCTION

This is a continuation-in-part of prior application Ser. No. 10/245,928 filed Sep. 18, 2002 which is a continuation in part of Ser. No. 10/105,722 filed Mar. 25, 2002 now U.S. Pat. No. 6,918,906 which claims priority to provisional application No. 60/280,009 filed Mar. 30, 2001. This application incorporates by reference U.S. Ser. No. 10/245,928 and U.S. Ser. No. 10/105,722. This application incorporates by reference Ser. No. 10/245,928 and Ser. No. 10/105,722.

FIELD OF THE INVENTION

The present invention relates, in general, to medical devices, such as for us in the esophagus and GI tract for ablation, and more particularly to medical devices having improved wall constructions.

BACKGROUND OF THE INVENTION

Gastro-esophageal reflux disease (GERD), which is associated with severe heartburn, affects a substantial portion of the world population. People who experience heartburn at least once a week are reportedly at an increased risk of developing esophageal cancer in their lifetime. When left untreated, chronic GERD can cause the inner lining of the esophagus to change from squamous mucosa to columnar mucosa, which sometimes includes intestinal metaplasia or Barrett's esophagus. Left untreated, Barrett's esophagus can progress to esophageal cancer, for which a common surgical treatment is esophagectomy (removal of the esophagus.)

Accordingly, scientists and engineers continue to seek improved medical instruments for treating diseased tissue in the esophagus.

SUMMARY OF THE INVENTION

Applicant has recognized the need for providing a medical instrument for use in the esophagus and GI tract which has sufficient bending flexibility for permitting comfortable insertion of the instrument into the patient's esophagus, while having sufficient torsional stiffness so permit a doctor or ocher operator to accurately position a distal portion of the medical device adjacent a tissue site to be treated.

In one embodiment, the present invention provides an ablation device having a laminate elongate hollow member and at least one electrode disposed distally of the laminate member. The laminate member can comprise a corrugated tube and an outer layer disposed radially outwardly of the corrugated tube. One or more electrical conductors for providing energy to the electrode can be disposed intermediate the corrugated tube and the outer layer.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 8 is a sectional view of the distal end of the endoscopic ablation system illustrated in FIG. 7.

FIG. 9 is a sectional view taken at line 9—9 of the endoscopic ablation system illustrated in FIG. 8.

FIG. 10 is a sectional view taken at line 10—10 of the endoscopic ablation system illustrated in FIG. 8.

FIG. 18 is a sectional view of the distal portion of the endoscopic ablation system shown in FIG. 17, wherein a plurality of electrodes 28 are mounted on the tapered end cover 84 near a distal tip 104.

FIG. 19 is a sectional view of the distal portion of the endoscopic ablation system shown in FIG. 17, wherein a plurality of electrodes 28 are mounted on a rigid support member 26.

FIG. 27 is a sectional view of the distal portion of an endoscopic ablation system 11 that includes an image sensor 120.

FIG. 28 is a side view of the distal portion of endoscopic ablation system 11 shown in FIG. 27, with a detachable ablation cap 146 removed from a flexible shaft 138.

DETAILED DESCRIPTION OF THE INVENTION

Figure 1:
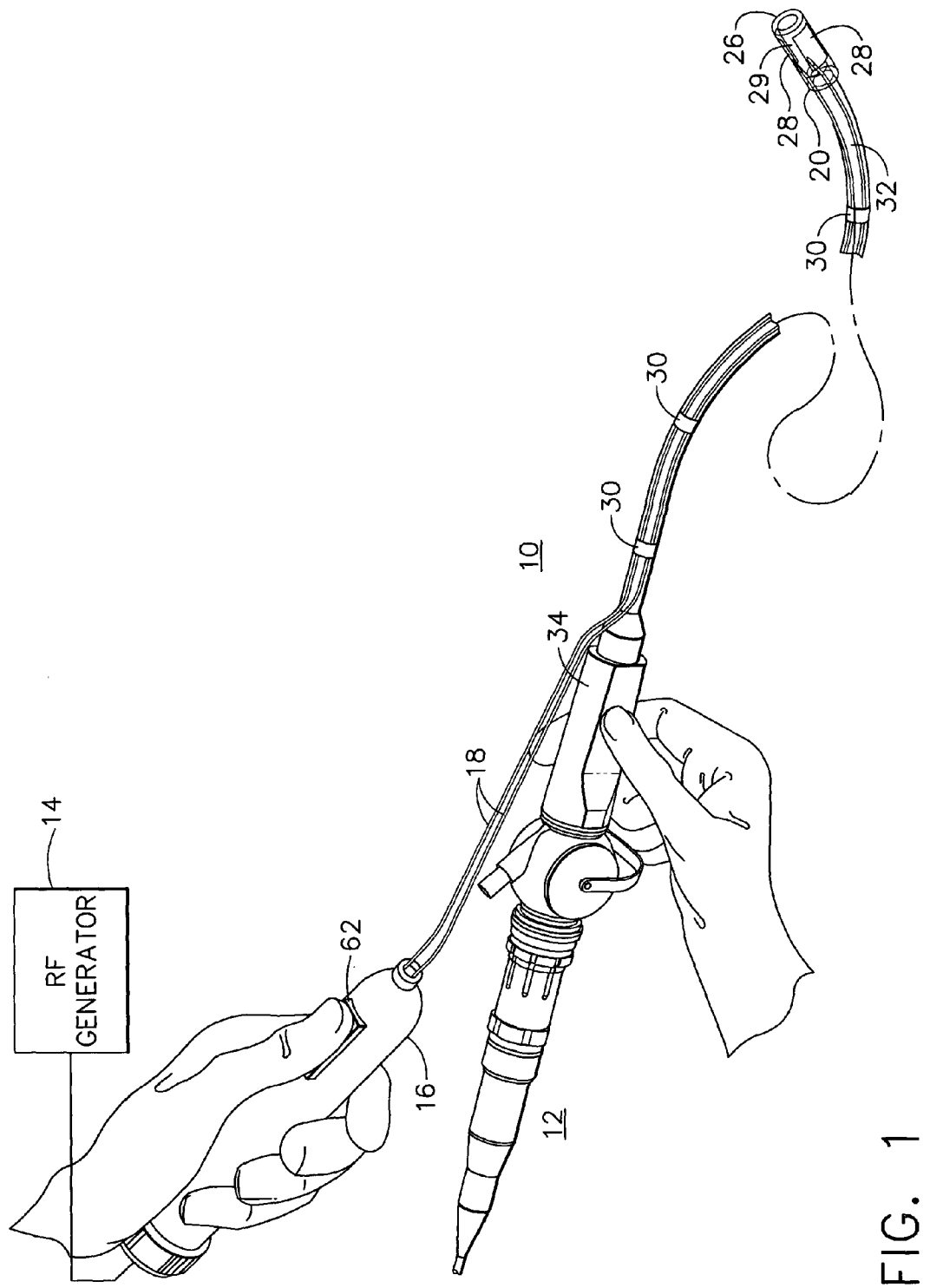
FIG. 1 is an illustration of an endoscopic ablation system mounted on a flexible endoscope.

FIG. 1 shows an endoscopic ablation system 10 mounted on a flexible endoscope 12 (also referred to as endoscope 12), such as the GIF-100 model available from Olympus Corporation. Flexible endoscope 12 includes an endoscope handle 34 and a flexible shaft 32. Endoscopic ablation system 10 generally comprises an ablation cap 20, a plurality of conductors 18, a handpiece 16 having a switch 62, and an RF (radio frequency) generator 14. Ablation cap 20 fits over the distal end of flexible shaft 32 and conductors 18 attach to flexible shaft 32 using a plurality of clips 30. Ablation cap 20 includes a rigid support member 26, a plurality of electrodes 28, and a viewing window 29 positioned between electrodes 28. In this embodiment, rigid support member 26 is made of a transparent material such as polycarbonate and viewing window 29 is the portion of rigid support member 26 between electrodes 18. Manual operation of switch 62 of handpiece 16 electrically connects or disconnects electrodes 18 to RF generator 14. Alternatively, switch 62 may be mounted on, for example, a foot switch (not shown).

RF generator 14 is a conventional, bipolar/monopolar electrosurgical generator such as one of many models commercially available, including Model Number ICC 350, available from Erbe, GmbH. Either the bipolar mode or the monopolar mode may be used for the present invention. When using the bipolar mode with two electrodes 18 on ablation cap 20, one electrode is electrically connected to one bipolar polarity, and the other electrode is electrically connected to the opposite bipolar polarity. If more than two electrodes 18 are used, polarity of electrodes 18 is alternated so that any two adjacent electrodes have opposite polarities.

When using the monopolar mode with two or more electrodes 18, a grounding pad is not needed on the patient. Because a generator will typical be constructed to operate upon sensing connection of ground pad to the patient when in monopolar mode, it can be useful to provide an impedance circuit to simulate the connection of ground pad to the patient. Accordingly, when the device of the present invention is used in monopolar mode without a grounding pad, an impedance circuit can be assembled by one of skilled in the art, and electrically connected in series with one of conductors 18 that would otherwise be used with a grounding pad during monopolar electrosurgery. Use of the impedance circuit allows use of the generator in monopolar mode without use of a grounding pad attached to the patient.

The optimal power level required to operate endoscopic ablation system 10 of the present invention is approximately in the range of 10–50 watts, although endoscopic ablation system 10 is also functional at lower or higher power levels.

Figure 2:
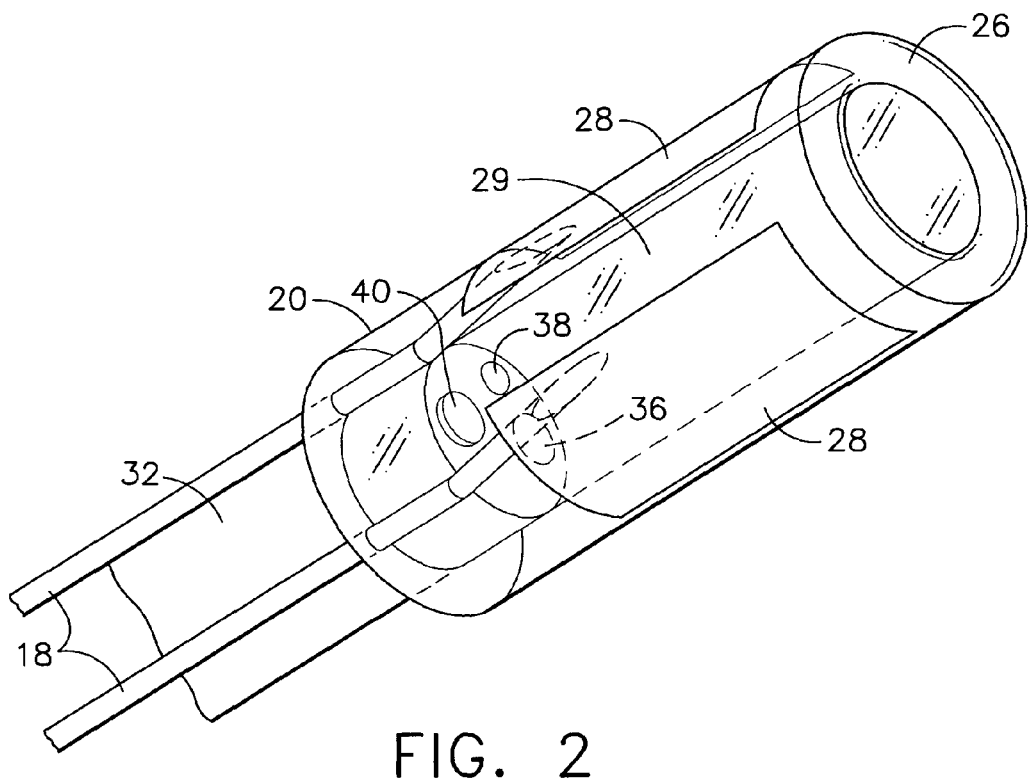
FIG. 2 is an enlarged view of an ablation cap at the distal end of the endoscopic ablation system illustrated in FIG. 1.

FIG. 2 is an enlarged view of ablation cap 20 of endoscopic ablation system 10 shown in FIG. 1. Ablation cap 20 fits securely over the distal end of flexible shaft 32. Electrodes 28 are positioned on the outside surface of rigid support member 26, which has a circular cylinder shape in this embodiment. Rigid support member 26 may also have alternate cylindrical shapes, including shapes in which at least a portion of the cross sectional perimeter is non-arcuate. For example, rigid support member 26 may have a "D-shape" cross-section, where electrodes 28 are positioned on the flat portion of the "D-shape." Conductors 18 are electrically insulated from each other and surrounding structures, except for electrical connections such as to electrodes 28. The distal end of flexible shaft 32 of flexible endoscope 12 includes a light source 40, a viewing port 38, and a working channel 36. Viewing port 38 transmits an image within its field of view to an optical device such as a CCD camera within flexible endoscope 12 so that an operator may view the image on a display monitor (not shown). In the embodiment shown in FIG. 2, the distal end of flexible shaft 32 is proximal to electrodes 28 and viewing window 29, enabling the operator to see tissue between electrodes 28 through viewing window 29.

Figure 3:
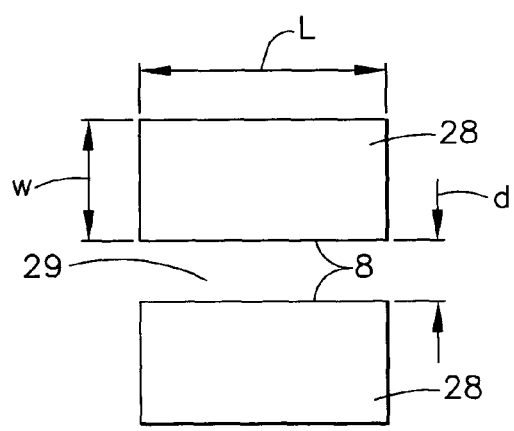
FIG. 3 is a geometric diagram showing the relative size and position of two adjacent electrodes that would be mounted on the ablation cap illustrated in FIG. 2.

FIG. 3 shows the geometric relationship of a particular embodiment of electrodes 28. In this embodiment, two rectangular electrodes 28, each having a width "w" and a length "L", have parallel, adjacent edges 8 that are separated by a distance "d". This geometric relationship may be used to calculate an ablation index, which has particular significance to the location, size, shape, and depth of ablation achievable, as will be described later. Viewing window 29 (see FIG. 2) is approximately defined by the d×L rectangular area between electrodes 28.

Figure 4:
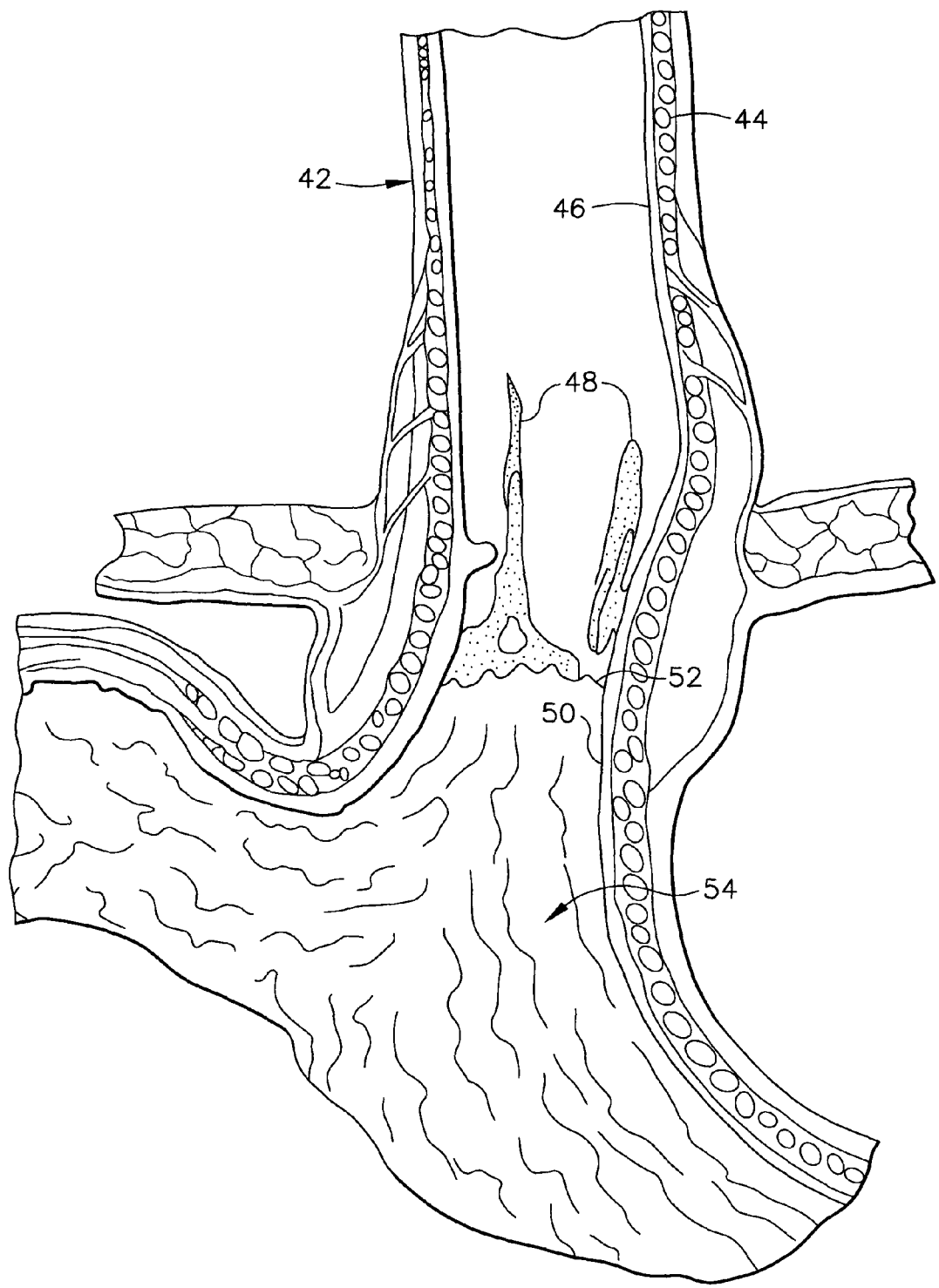
FIG. 4 is a sectional view of the lower esophagus and the upper stomach of a human being.

FIG. 4 is a sectional view of the lower end of an esophagus 42 and the upper portion of a stomach 54 of a human being. Esophagus 42 has a mucosal layer 46, a muscular layer 44, and a region of diseased tissue 48. The boundary between mucosal layer 46 of esophagus 42 and a gastric mucosa 50 of stomach 54 is a gastro-esophageal junction 52, which is approximately the location for the lower esophageal sphincter (LES). The LES allows food to enter the stomach 54 while preventing the contents of stomach 54 from refluxing into lower esophagus 42 and damaging mucosal layer 46. Diseased tissue 48 can develop when chronic reflux is not treated. In one form, diseased tissue 48 may be, for example, intestinal metaplasia, which is an early stage of Barrett's esophagus. As can be seen in FIG. 4, the esophagus is relatively flaccid and contains numerous folds and irregularities on the interior lining.

Figure 5:
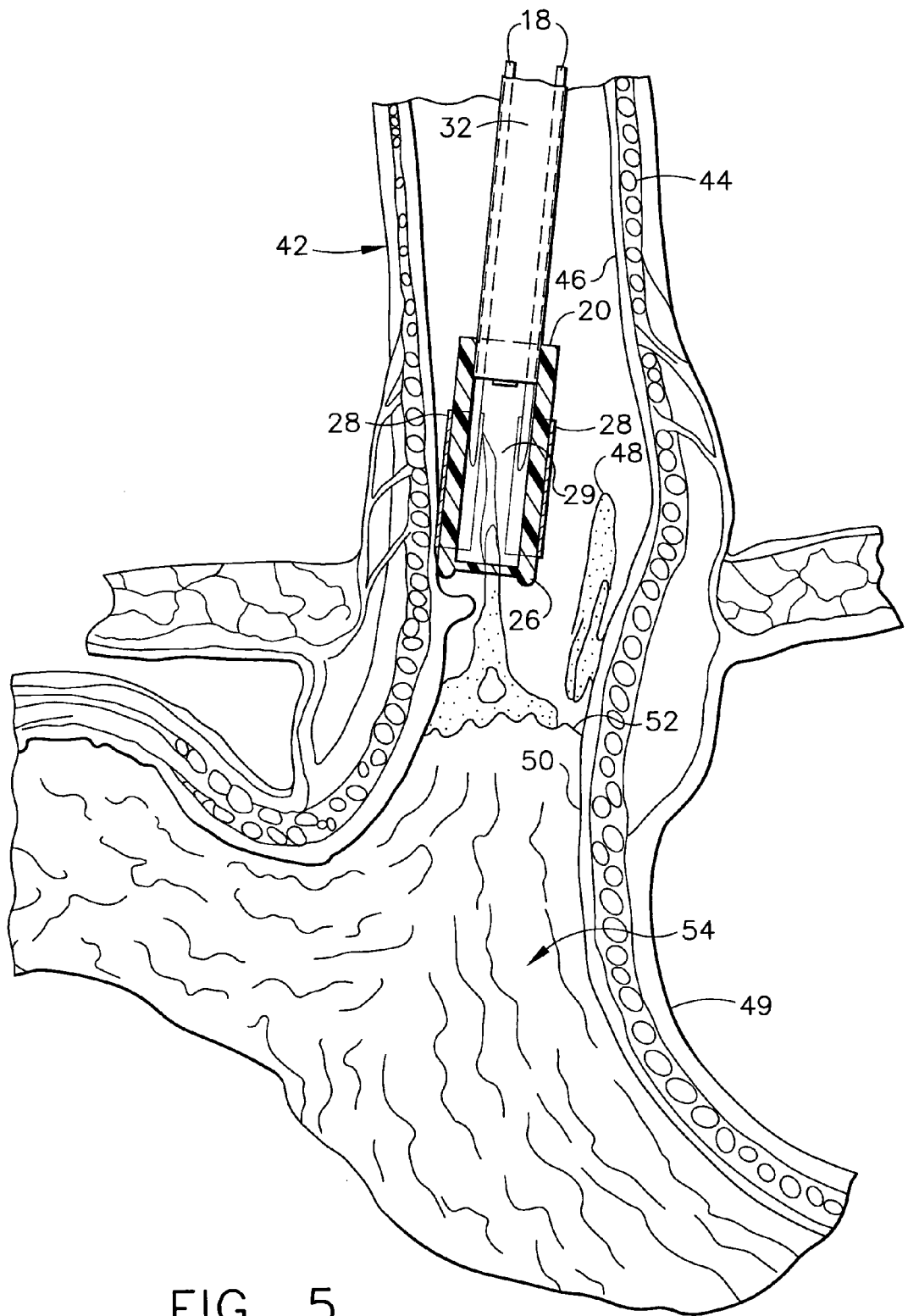
FIG. 5 illustrates the use of the endoscopic ablation system of FIG. 1 to treat tissue at the lower esophagus.

FIG. 5 illustrates the use of endoscopic ablation system 10 to treat diseased tissue 48 in lower esophagus 42. The operator positions ablation cap 20 using endoscopic visualization so that diseased tissue 48 to be treated lies under viewing window 29.

Figure 6:
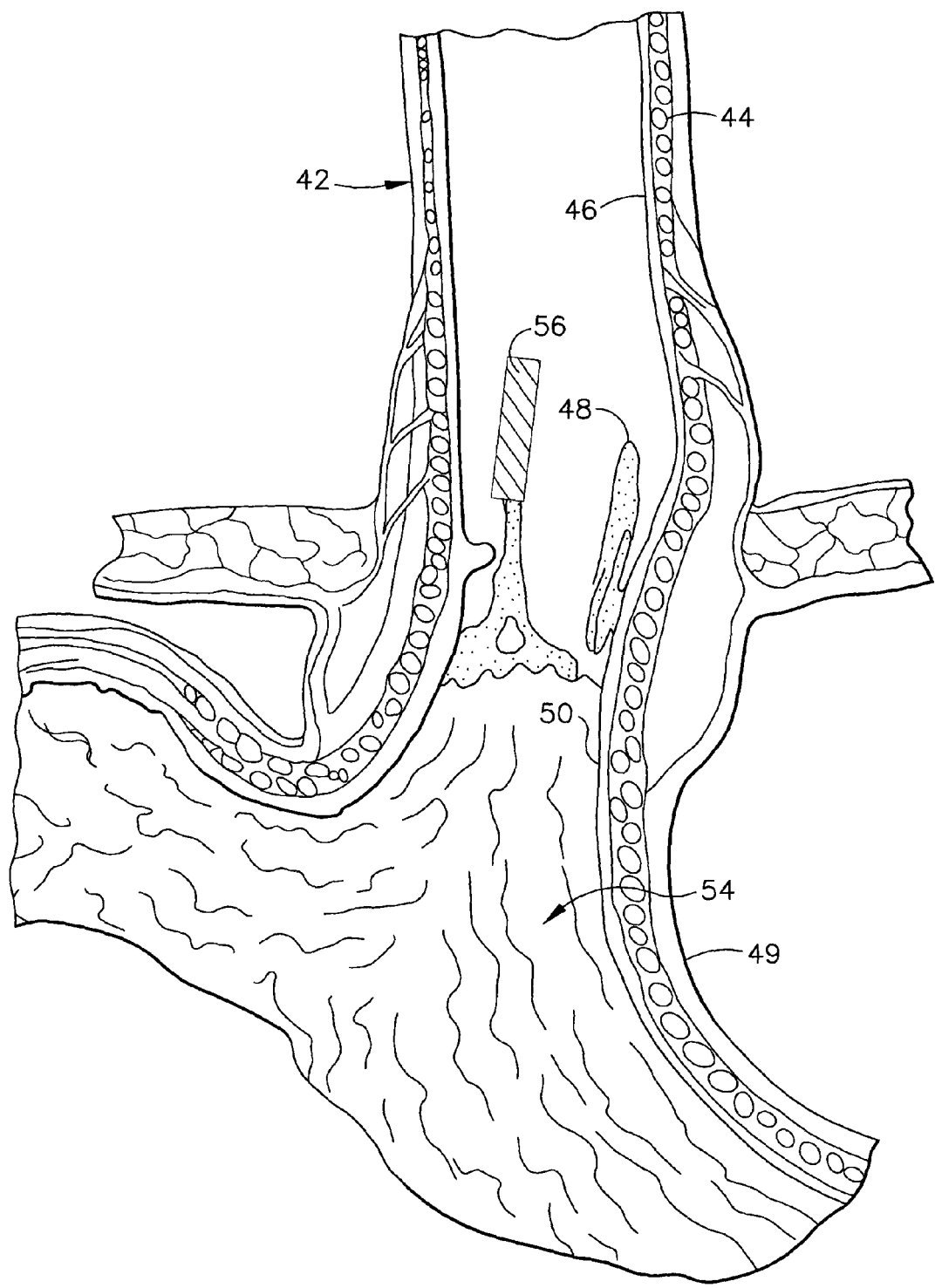
FIG. 6 is sectional view of the lower esophagus showing tissue that has been treated using the endoscopic ablation system of FIG. 1.

FIG. 6 is sectional view of lower esophagus 42 showing tissue that has been treated using endoscopic ablation system 10 according to the present invention. In FIG. 6, the size and shape of the treated tissue 56 substantially corresponds to the size and shape of viewing window 29.

The operator may treat diseased tissue 48 using the embodiment of endoscopic ablation system 10 of the present invention shown in FIGS. 1 and 5 as follows. The operator inserts flexible shaft 32 of endoscope 12 into lower esophagus 42 trans-orally. Rigid support member 26 holds lower esophagus 42 open as the operator uses endoscopic visualization through ablation cap 26 to position electrodes 28 next to the diseased tissue 48 to be treated. Rigid support member 26 opens and supports a portion of the flaccid, lower esophagus 42 and helps to bring the tissue to be treated into intimate contact with electrodes 28 and viewing window 29. While watching through viewing window 29, the operator actuates switch 62, electrically connecting electrodes 28 to RF generator 14 through conductors 18. Electric current then passes through the diseased tissue positioned in viewing window 29. When the operator observes that the tissue in viewing window 29 has been ablated sufficiently, the operator deactuates switch 62 to stop the ablation. The operator may reposition electrodes 28 for subsequent tissue treatment, or may withdraw ablation cap 26 (together with flexible endoscope 12). As illustrated in FIG. 6, treated tissue 56 has substantially the same width and length as viewing window 29.

Figure 7:
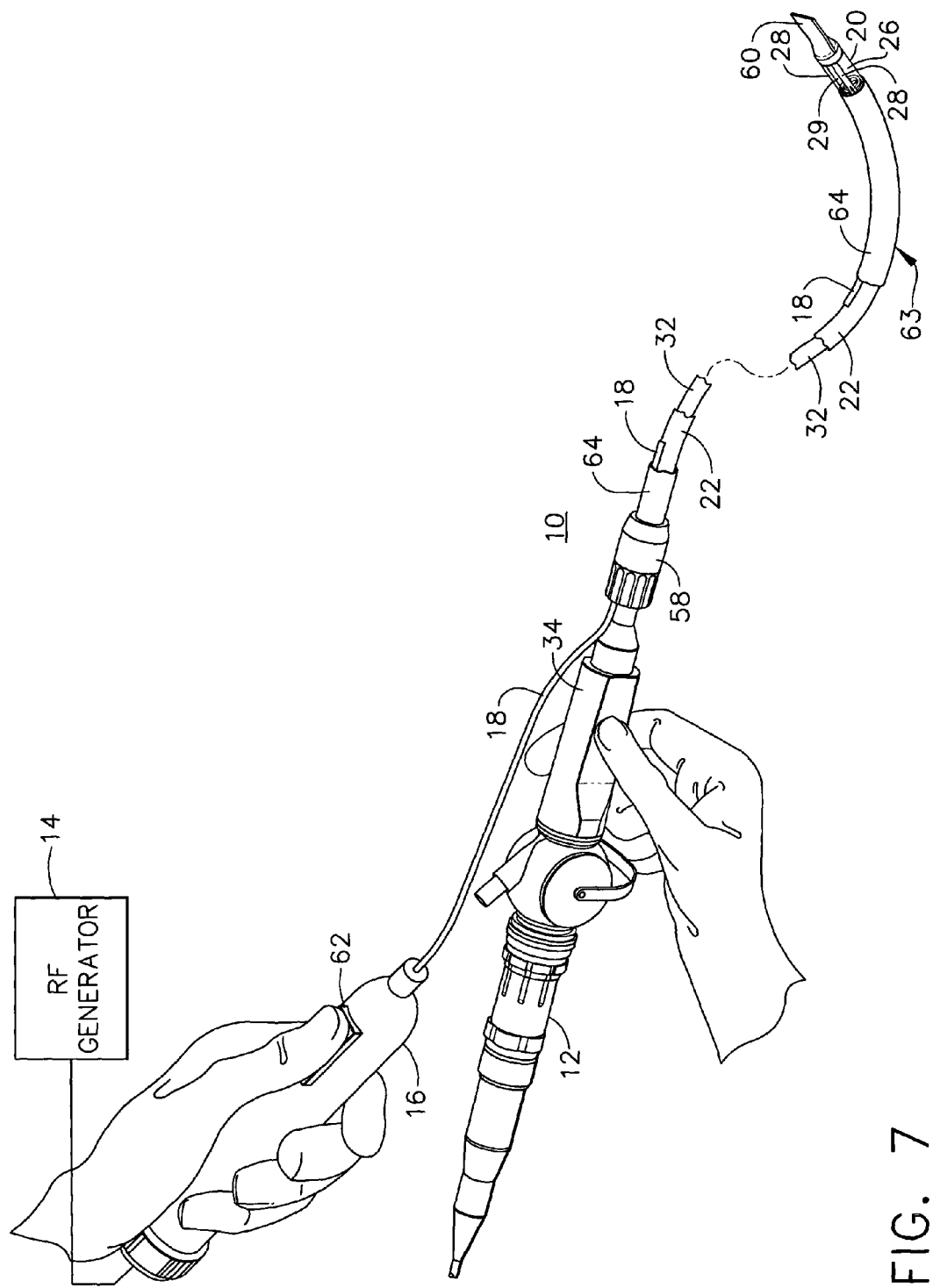
FIG. 7 illustrates an alternative embodiment of an endoscopic ablation system, which includes a rotation knob 58 and a valve 60 (also referred to as a tapered end cover).

FIG. 7 shows an alternate embodiment of an endoscopic ablation system 10 and generally comprises an ablation cap 20, a sheath 63, a pair of conductors 18, a handpiece 16 having a switch 62, and an RF generator 14. An operator may rotate ablation cap 20 around flexible shaft 32 of flexible endoscope 12 by manipulation of a rotation knob 58, which connects to sheath 63. Ablation cap 20 includes a rigid support member 26, at least two electrodes 28, and at least one viewing window 29 (between each pair of adjacent electrodes). Sheath 63 comprises a rotation tube 22 covered by an external tube 64. Ablation cap 20 attaches directly to the distal end of sheath 63. Rotation tube 22 can be made from a material such as, for example, corrugated polyethylene tubing, and fits slidably over a conventional, flexible endoscope. External tube 64 is preferably made from a heat-activated shrink tube material such as polyolefin. Conductors 18 are spirally wrapped around rotation tube 22 prior to assembling and shrinking external tube 64 onto rotation tube 22, thereby tightly retaining conductors 18 in the wound configuration. In the embodiment shown in FIG. 7, a valve 60 (also referred to as a tapered end cover), which may be, for example, a duck bill valve, connects to the distal end of rigid support member 26. Valve 60 allows an operator to extend the distal end of flexible endoscope 12 beyond the distal end of rigid support member 26 to improve visualization of tissue structures, especially during intubation. The operator may also retract the distal end of flexible endoscope 12 within rigid support member 26 to allow visualization of viewing window 29 and electrodes 28, while preventing bodily fluids from entering rigid support member 26 and impairing visualization by contact with flexible endoscope 12.

Alternate embodiments of valve 60 may be envisioned by those skilled in the art, each embodiment being particularly adapted to the medical procedure and anatomical structures involved. For example, in an alternative embodiment of the present invention, the distal end of valve 60 could be further tapered and elongated to allow for easier insertion into the esophagus. Valve 60 could further be transparent to enable the physician to visualize through valve 60 during intubation into the esophagus, while preventing contact of bodily fluids against the distal end of flexible endoscope 12.

FIG. 8 is a sectional view taken along the longitudinal axis of endoscopic ablation system 10 of FIG. 7. The distal portion of flexible shaft 32 is inside rotation tube 22 of endoscopic ablation system 10. A pair of conductors 18 passes through a strain relief 66 of rotation knob 58 and between external tube 64 and rotation tube 22. Each conductor 18 connects electrically to one of electrodes 28 on ablation cap 20. Rotation tube 22 rotatably joins rotation knob 58 to ablation cap 20, enabling the operator to rotatably orient electrodes 28, even after insertion into the esophagus, by remotely actuating rotation knob 58. The distal end of flexible shaft 32 extends from the distal end of sheath 63 into ablation cap 20 and proximal to electrodes 18. A viewing window 29 between electrodes 28 is within the field of view of flexible endoscope 12, thus enabling the operator to see on a display monitor the tissue that is located between electrodes 18. Valve 60 extends from the distal end of ablation cap 20 to prevent tissue or fluids from entering ablation cap 20.

FIG. 9 is a sectional view taken along line 9—9 of ablation cap 20 of endoscopic ablation system 10 of FIG. 8. Conductors 18 connect to electrodes 28 with the portion of rigid support member 26 between electrodes 28 defining viewing window 29. Rotation tube 22 retains flexible shaft 32. The inside diameter of rotation tube 22 is larger than the outer diameter of flexible endoscope 12 to allow rotation of rotation tube 22 while holding flexible endoscope 12 stationary, or vice versa. In this embodiment at least the portion of rigid support member 26 that forms viewing window 29 is transparent so that the operator may endoscopically view the tissue between electrodes 28. Flexible endoscope 12 includes a light source 40, a viewing port 38, and a working channel 36.

FIG. 10 is a sectional view taken along line 10—10 of rotation tube 22 of endoscopic ablation system 10 of FIG. 8. External tube 64 and rotation tube 22 assemble and retain conductors 18 as already described. Light source 40, viewing port 38, and working channel 36 of flexible endoscope 12 are shown.

Figure 11:
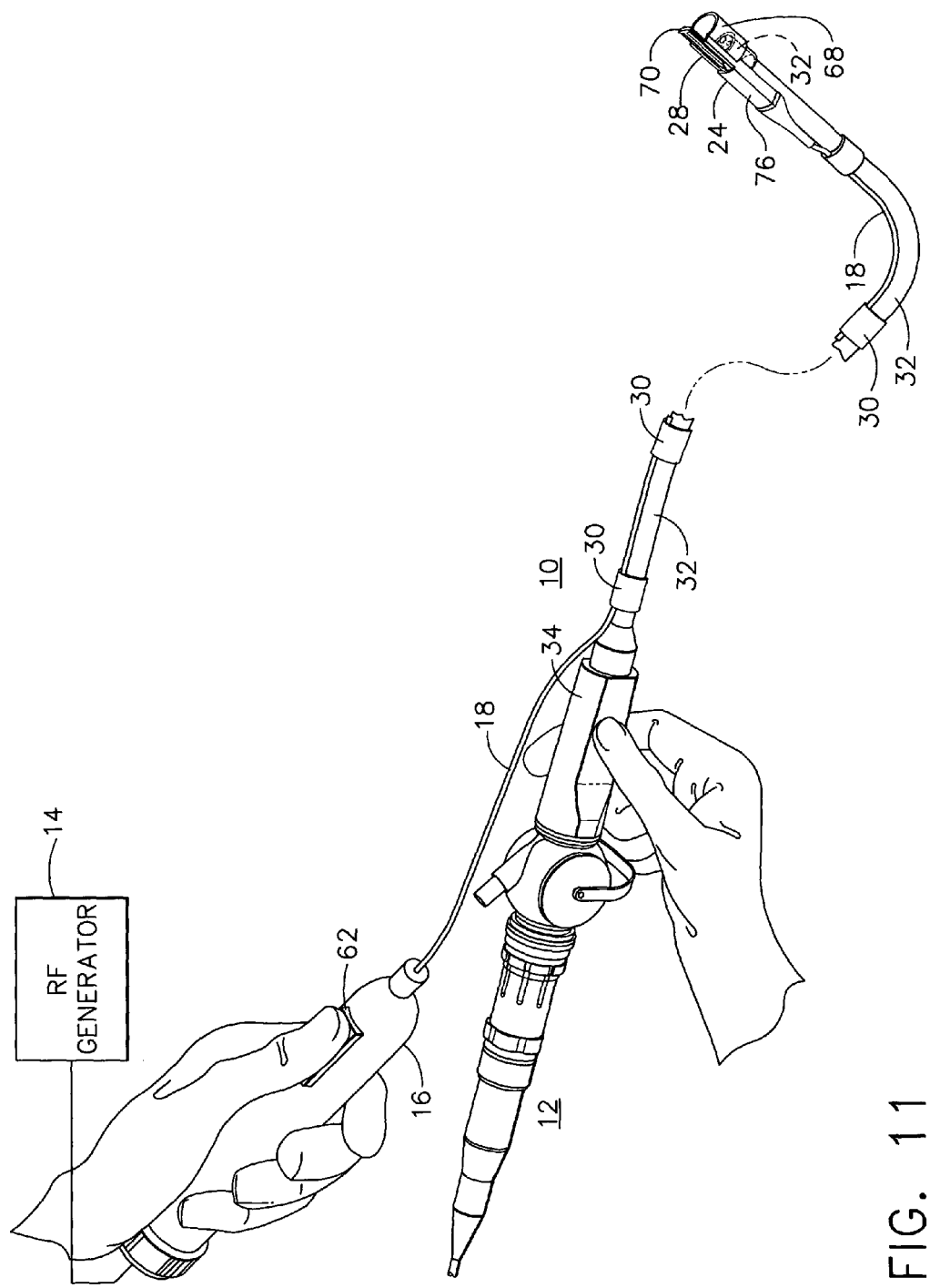
FIG. 11 is an illustration of a further embodiment of an endoscopic ablation system, which includes an electrode sled 70.

FIG. 11 shows a further embodiment of an endoscopic ablation system 10 according to the present invention. A flexible ablation cap 24 includes a flexible support member 68 and at least two electrodes 28 mounted on an electrode sled 70, which may be housed in or extended from a sled housing 76. Flexible ablation cap 24 mounts over the distal end of flexible shaft 32. Conductors 18 electrically connect to electrodes 28 as in the previous embodiments, and may be attached to flexible shaft 32 by a plurality of clips 30. Again, conductors 18 electrically connect to RF generator 14 by a switch 62 of a handpiece 16.

Figure 12:
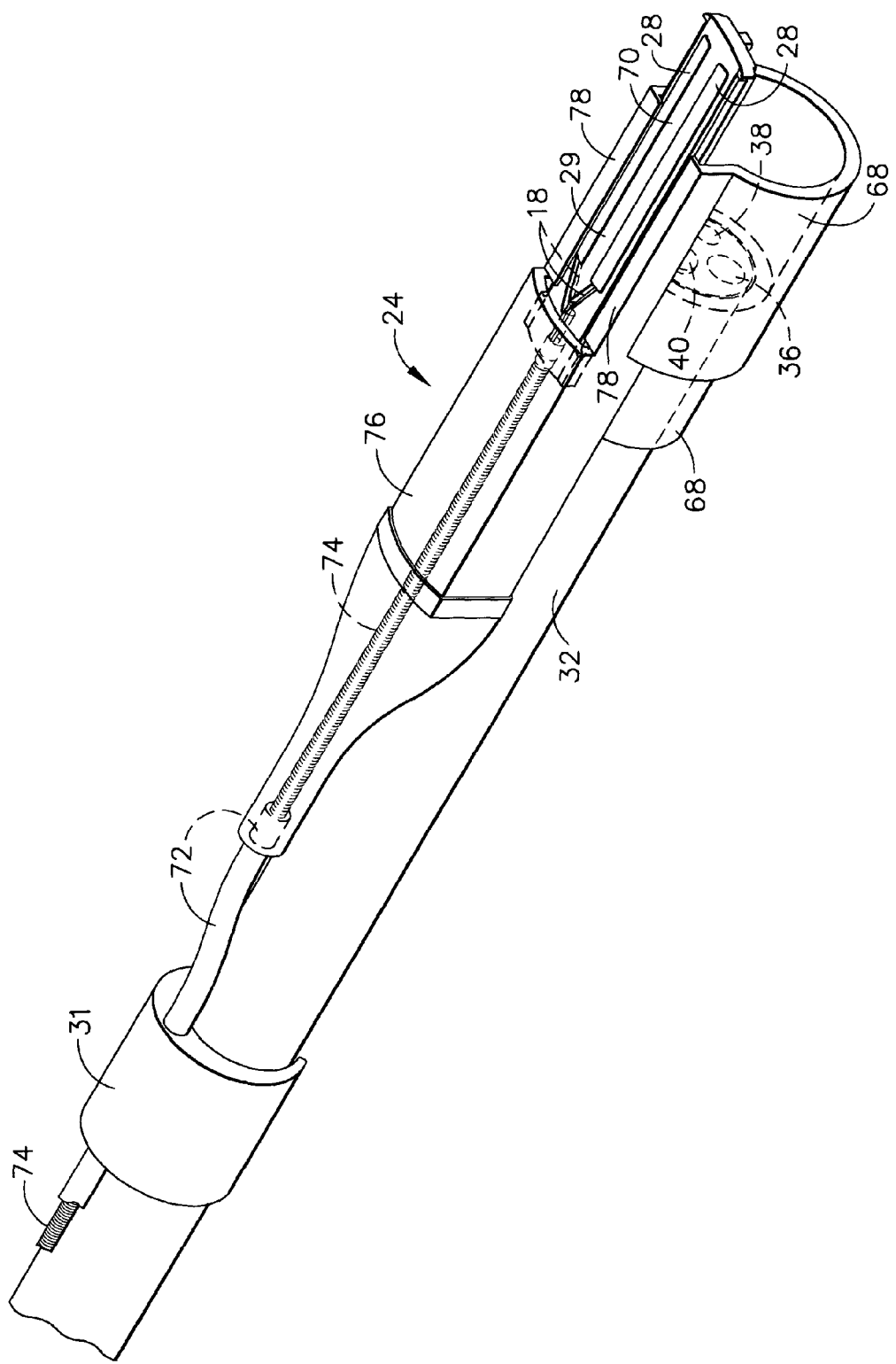
FIG. 12 is an enlarged, perspective view of the distal portion of the endoscopic ablation system illustrated in FIG. 11, showing electrode sled 70 in an extended position.

FIG. 12 is an enlarged view of flexible ablation cap 24 of the endoscopic ablation system 10 illustrated in FIG. 11 with electrode sled 70 fully extended. A sled housing 76 is a soft and flexible, pouch-like container, which may be made of a material such as PTFE in order to prevent damage to the mucosa as the operator introduces endoscopic ablation system 10 into the esophagus. Sled housing 76 and flexible support member 68 may be molded as a single piece. Electrode sled 70 may be made of a clear rigid material such as, for example, polycarbonate. As shown in FIG. 12, electrode sled 70 includes two electrodes 28, a viewing window 29, and two conductors 18. At least the portion of electrode sled 70 that forms viewing window 29 is transparent to allow the operator to view endoscopically the tissue between electrodes 28. Flexible support member 68 includes sled guides 78, which are adapted to receive electrode sled 70. Extension of sled 70 to an extended position stiffens flexible support member 68 such as may be desired during ablation; retraction of sled 70 to a retracted position allows flexible support member 68 to flex such as may be desirable during intubation. A drive cable 74 retains conductors 18, which extends proximally through sled housing 76 and into a sleeve 72. Sleeve 72 attaches to flexible shaft 32 by a fixed clip 31. Thus, by extending drive cable 74, electrode sled 70 moves distally and, by retracting drive cable 74, electrode sled 70 moves proximally into sled housing 76.

Figure 13:
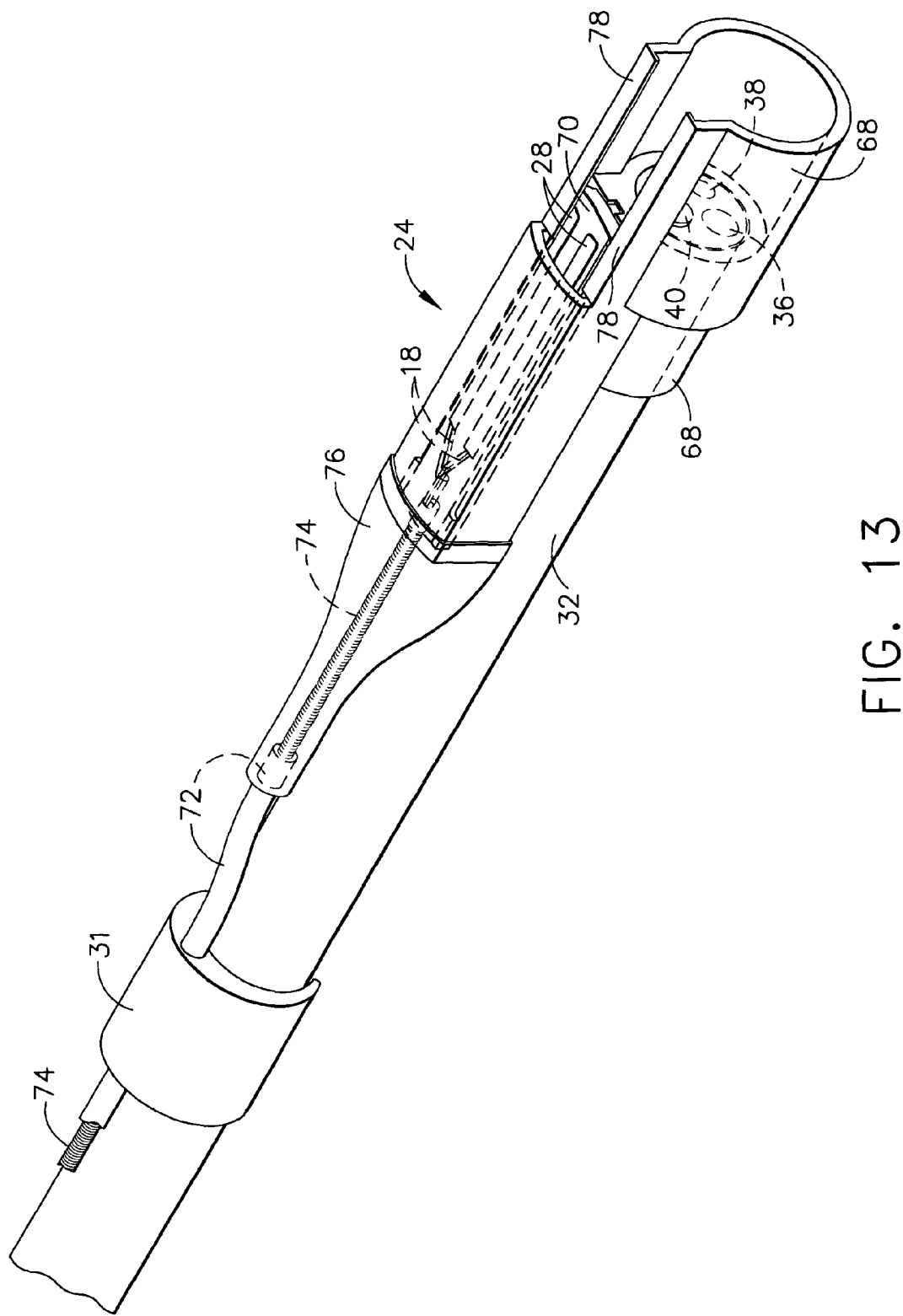
FIG. 13 is an enlarged, perspective view of the distal portion of the endoscopic ablation system illustrated in FIG. 11, showing electrode sled 70 in a retracted position.

FIG. 13 shows flexible ablation cap 24 of endoscopic ablation system 10 of FIG. 11 with electrode sled 70 retracted into sled housing 76, or in a retracted position.

Figure 14:
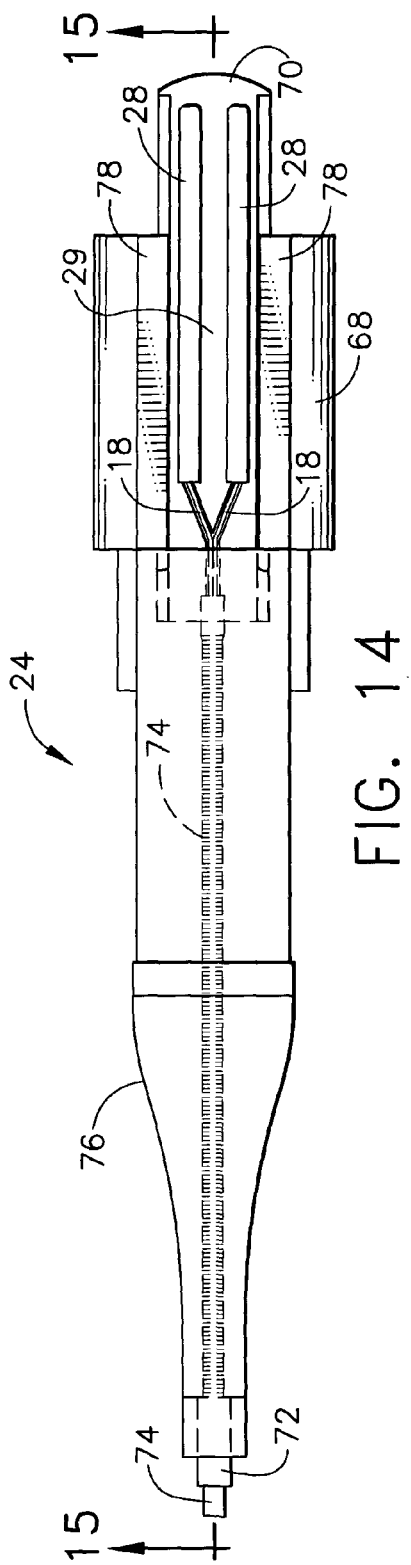
FIG. 14 is an enlarged, top view of the distal portion of the endoscopic ablation system illustrated in FIG. 11, showing electrode sled 70 in the extended position.
Figure 15:
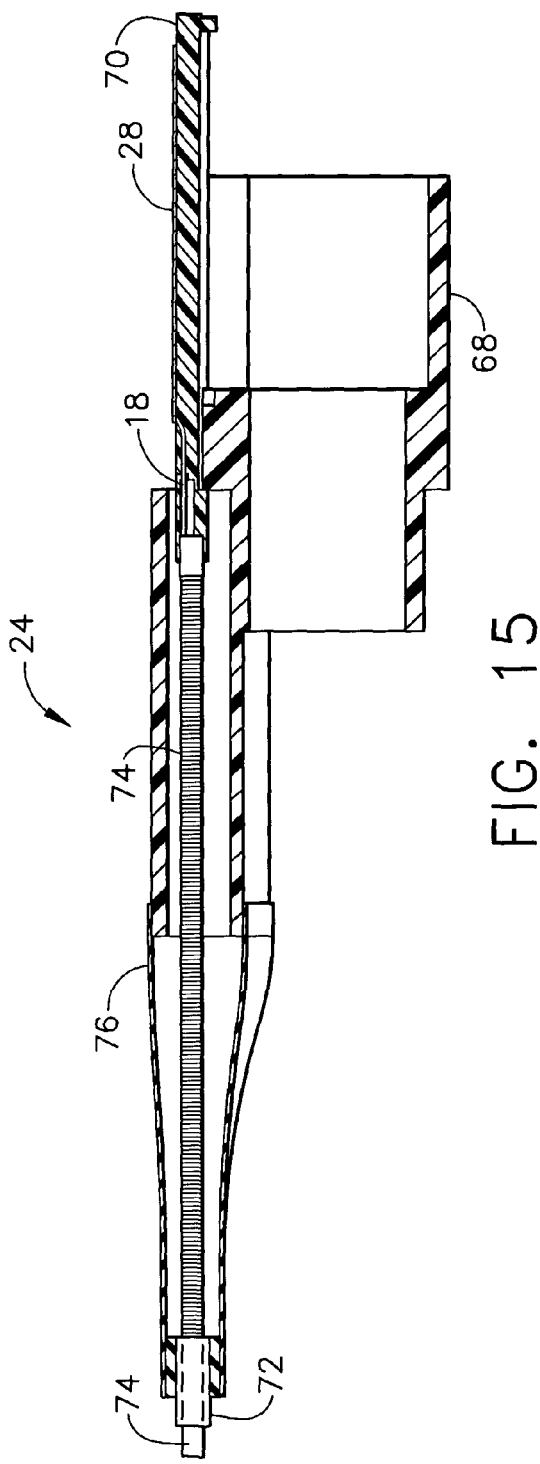
FIG. 15 is an enlarged, sectional side view of the distal portion of the endoscopic ablation system illustrated in FIG. 11, showing electrode sled 70 in the extended position.
Figure 16:
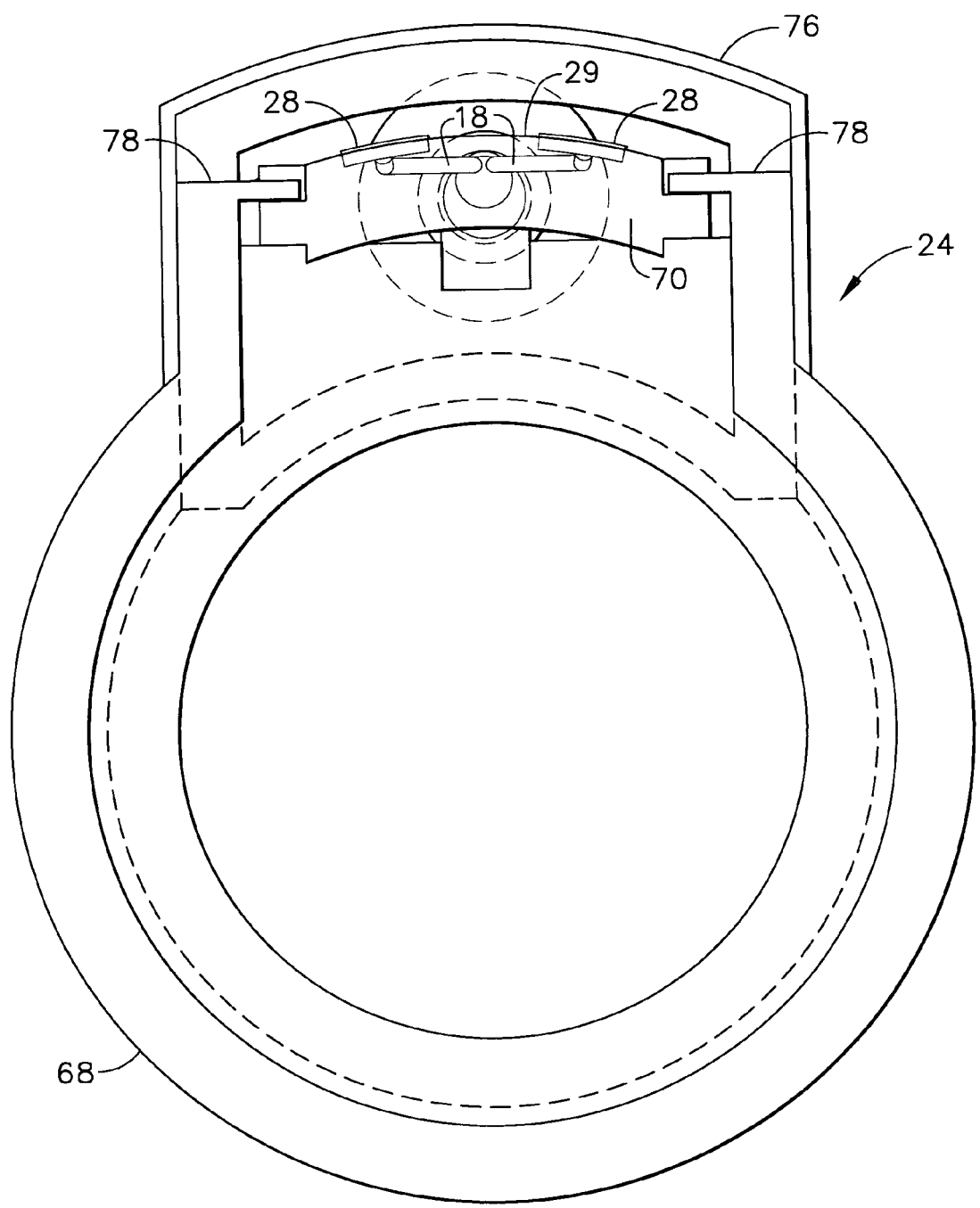
FIG. 16 is an enlarged, end view of the distal portion of the endoscopic ablation system illustrated in FIG. 11.

FIGS. 14–16 are additional views of flexible ablation cap 24 illustrated in FIG. 11. FIG. 14 is a top view of flexible ablation cap 24 with electrode sled 70 in an extended position. FIG. 15 is a side view of flexible ablation cap 24 with electrode sled 70 in an extended position. In FIGS. 14 and 15 electrode sled 70 includes electrodes 28, viewing window 29 and conductors 18, which are connected to electrodes 28. Flexible support member 68 includes sled guides 78. Drive cable 74, which houses conductors 18, is in turn housed within sled housing 76 and extends proximally into sleeve 72. FIG. 16 is an end view of the flexible ablation cap 24 of the endoscopic ablation system 10 illustrated in FIG. 11. FIG. 16 illustrates the arrangement of sled guides 78 and the engagement of electrode 70 by sled guides 78.

Figure 17:
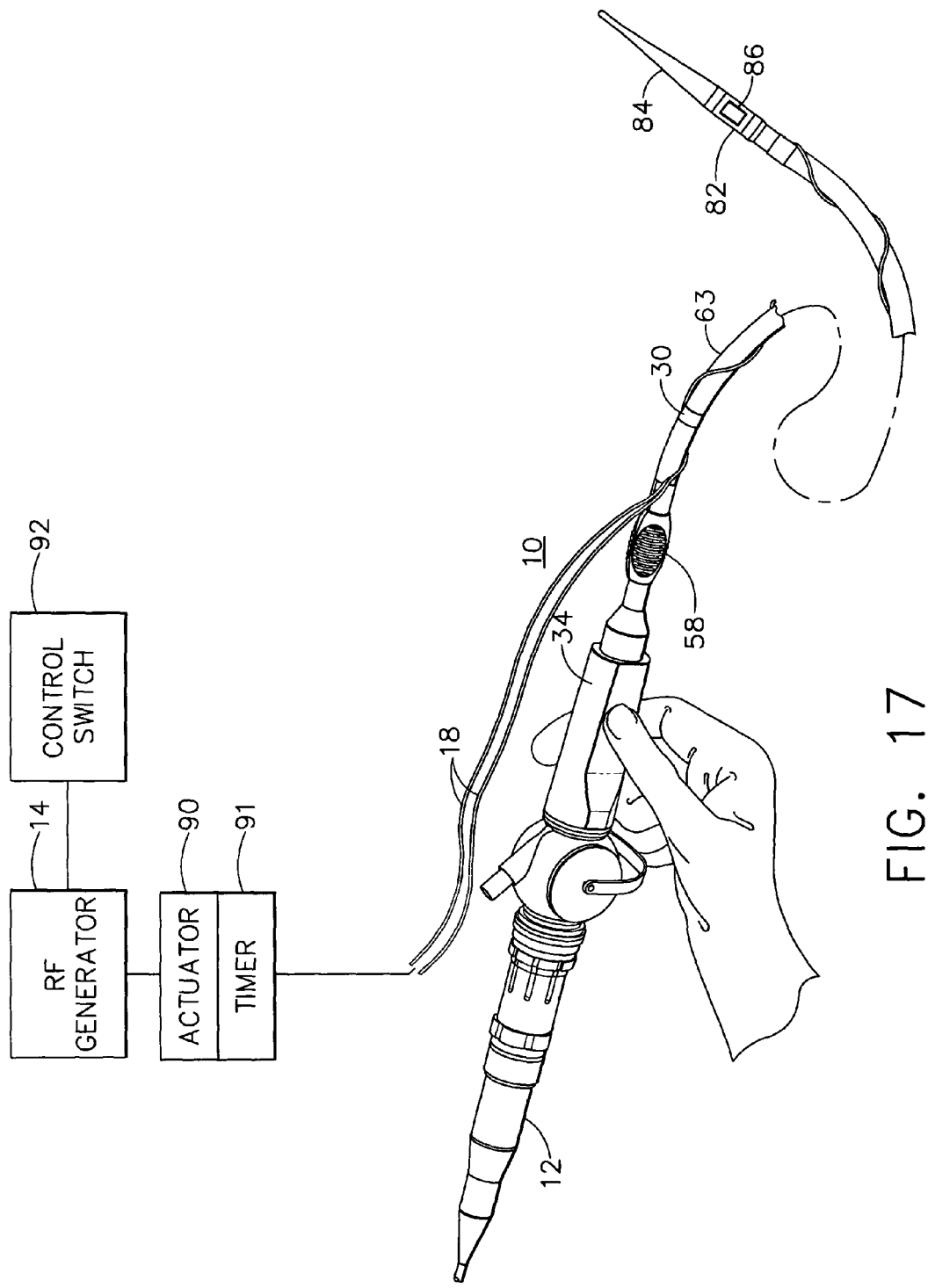
FIG. 17 is an illustration of a further embodiment of an endoscopic ablation system, which includes a tapered end cover 84 and a timer 91.

FIG. 17 is an illustration of a further embodiment of an endoscopic ablation system 10 for use with an endoscope 12 having an endoscope handle 34. Endoscopic ablation system 10 generally comprises a rotation knob 58, a sheath 63, an ablation cap 82, and a tapered end cover 84. Ablation cap 82 further includes an ablation cap-opening 86. Conductors 18 spirally wrap around the outside of sheath 63 in this embodiment, and at least one clip 30 attaches conductors 18 to sheath 63. Endoscopic ablation system 10 further comprises an actuator 90 and a timer 91. A plurality of electrodes 28 (hidden in this view) on ablation cap 82 electrically connect, via a pair of conductors 18, to actuator 90. The operator actuates actuator 90 manually to enable timer 91 to electrically connect electrodes 28 to RF generator 14 for a predetermined period of time. The operator then actuates control switch 92, which may be a foot operated control switch commonly available with RF generators, to activate RF generator 14. When RF generator 14 is activated, timer 91 automatically connects RF generator 14 to electrodes 28 for a predetermined length of time. For the embodiments of an endoscopic ablation system described herein, an appropriate predetermined length of time is approximately in the range of 0.1 to 10 seconds, and is preferably about one second. However, the length of predetermined time may vary depending on the geometry of the electrodes, the power level used on the RF generator, the type of tissue being treated, and other factors. Timer 91 includes a conventional timer circuit that is connected in electrical series to the output of a RF generator 14 having a control switch 92. When the operator actuates control switch 92, the electrical current from RF generator 14 induces a secondary current inside of timer 91. This secondary current supplies and immediately activates the timer circuit of timer 91, thereby connecting the output of RF generator 14 to electrodes 28 via a relay inside of timer 91. After a predetermined period of time, the relay disengages automatically, therefore electrically disconnecting RF generator 14 from the electrodes 28. Therefore, the operator controls when electrodes 28 are energized to begin ablation of tissue, but timer 91 controls when ablation stops, even though the operator may still be activating control switch 92. Timer 91 ensures complete ablation of diseased tissue in the viewing window and greatly reduces the possibility of operator error associated with RF energy application.

Timer 91 and actuator 90 of FIG. 17 may be provided as a handle with a switch much like handle 16 and switch 62 of FIG. 1. Alternately, timer 91 and actuator 90 may be incorporated into a table top unit (not shown), combined with RF generator 14 and control switch 92, or electronically packaged in many other ways that are readily apparent to one skilled in the art. Actuator 90, timer 91, RF generator 14, and control switch 92 may comprise a reusable portion of endoscopic ablation system 10. The remaining portion that includes conductors 18, sheath 63, rotation knob 58, and ablation cap 82 may be provided, for example, as a relatively low cost, sterile device that is disposable after use on one patient.

Figure 20:
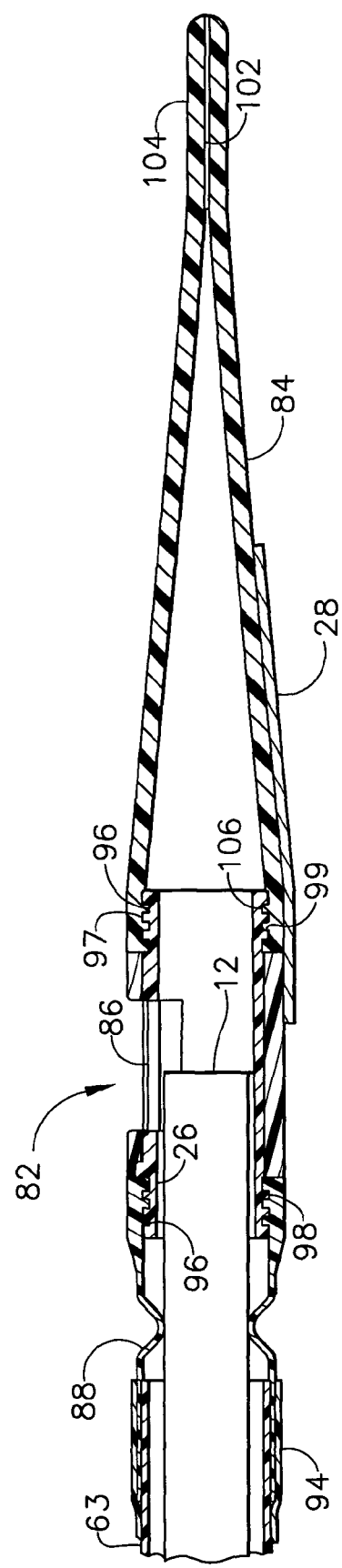
FIG. 20 is a sectional view of the distal portion of the endoscopic ablation system shown in FIG. 17, wherein a plurality of electrodes 28 are mounted partially on rigid support member 26 and partially on tapered end cover 84.

FIGS. 18, 19, and 20 are sectional views of the distal portion of endoscopic ablation system 10 shown in FIG. 17, and illustrate alternate locations of electrodes 28. FIGS. 18, 19, and 20 show the distal end of sheath 63 inserted into the proximal end of a flexible coupling 88 and attached by a ring 94 tightly compressed around sheath 63 and the proximal end of flexible coupling 88. The distal end of flexible coupling 88 attaches to the proximal end of a rigid support member 26 of ablation cap 82 by the engagement of a plurality of annular projections 96 on the inside of the distal end of flexible coupling 88 with a like plurality of annular grooves 98 formed into the proximal end of rigid support member 26. Flexible coupling 88 is made of a flexible tube material such as silicone rubber and allows low force angulation of sheath 63 with respect to ablation cap 82, thus facilitating passage of ablation cap 82 through the esophagus of the patient. The distal end of rigid support member 26 includes a plurality of annular grooves 99 for retaining a plurality of annular projections 97 on the inside of the proximal end of tapered end cover 84. Tapered end cover 84 is made of a transparent, flexible material such as, for example, clear or tinted polyurethane that is commonly used for flexible, extruded tubing. Tapered end cover 84 further includes an elongated, distal tip 104 that helps the operator to insert ablation cap 82 into the esophagus.

Tapered end cover 84 is hollow in order to allow positioning of the distal end of endoscope 12 partially into tapered end cover 84, as shown in FIG. 18. This enables the operator to view the interior of the esophagus, yet protects the distal end of endoscope 12 from tissue structures and bodily fluids that may impair visualization. Tapered end cover 84 is shaped like a bougie tube, which is commonly used by endoscopists for dilating the esophagus prior to intubation with an endoscope. Distal tip 104 of tapered end cover 84 includes a channel 102 so that the operator may pass a guide wire through ablation cap 82 and sheath 63, in order to facilitate positioning of ablation cap 82 inside of the esophagus.

As shown in FIGS. 18, 19, and 20, electrodes 28 may be mounted at varying locations on ablation cap 82. In FIG. 18, electrodes 28 are attached to the outside of tapered end cover 84 near distal tip 104. As indicated in FIG. 18, electrodes 28 are positioned on a portion of tapered end cover 84 that has a smaller cross-sectional diameter than the diameter of the distal end of endoscope 12. As shown in FIG. 19, electrodes 28 may also be attached to rigid support member 26, as was also described for the embodiments shown in FIGS. 1 and 7.

In FIG. 19, a portion of one of conductors 18 is shown as it may be electrically connected to one of electrodes 28 by a solder and/or compression connection. (Conductors 18 are not shown in FIGS. 18 and 20.) In FIG. 20, electrodes 28 are positioned partially on rigid support member 26 and partially on tapered end cover 84. Electrodes 28 may vary in size, shape, and position on ablation cap 82, as shown in the examples of FIGS. 18, 19, and 20, but importantly, still follow the geometric relationships described for FIG. 3 in order to achieve a desired ablation quality.

Still referring to FIGS. 18, 19, and 20, rigid support member 26 also includes side opening 86. In the examples shown, side opening 86 is rectangularly shaped and positioned between the distal end of flexible coupling 88 and the proximal end of tapered end cover 84. In the examples shown in FIGS. 19 and 20, side opening 86 is on the side of rigid support member 26 opposing the position of electrodes 26. Side opening 86 provides access to tissue structures next to ablation cap 82 with instrumentation passed through the working channel of endoscope 12. In addition, side opening 86 allows fluid communication between endoscope 12 (that normally includes suction and irrigation channels) and the interior of the esophagus around ablation cap 86. Therefore, the operator may position electrodes 28 adjacent to tissue to be ablated and apply the suction provided with endoscope 12. As the lumen size of the esophagus decreases under vacuum, the esophagus collapses around ablation cap 82, thus bringing the tissue to be treated in intimate contact with electrodes 28 and viewing window 29. This facilitates uniform electrode contact for even ablation, and improves endoscopic visualization through the viewing window of tissue being treated during the procedure.

Figure 21:
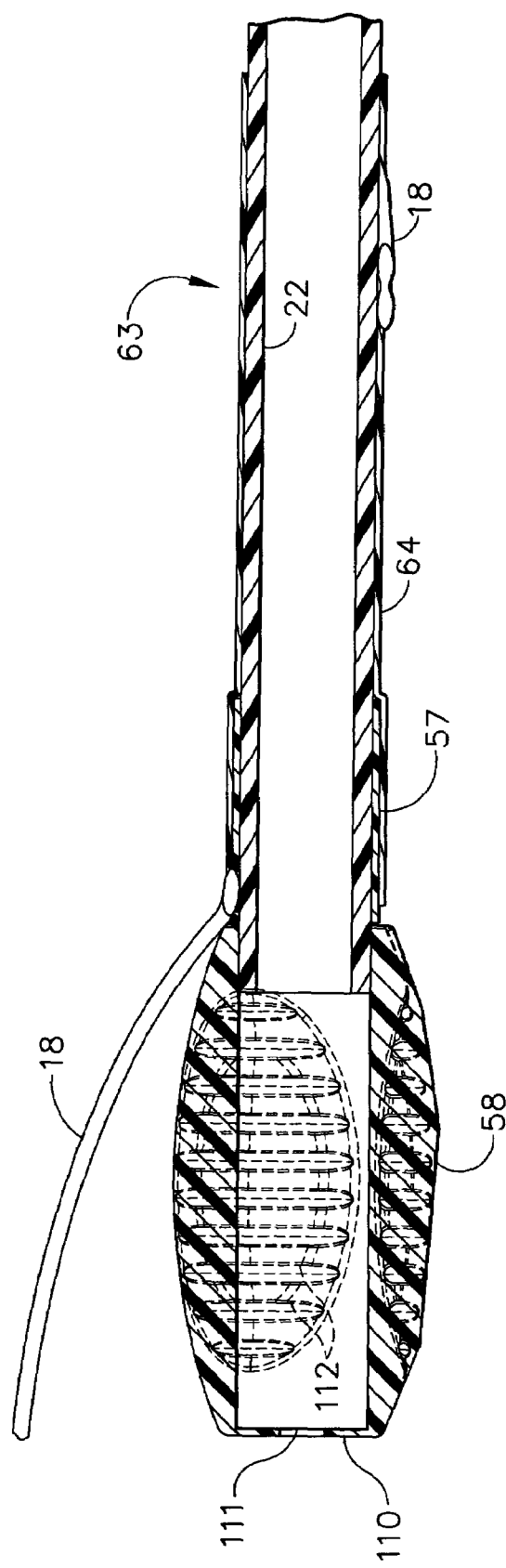
FIG. 21 is a sectional view of the proximal portion of the endoscopic ablation system shown in FIG. 17.

FIG. 21 is a sectional view of the proximal portion of sheath 63, rotation knob 58, and conductors 18 of the endoscopic ablation system 10 shown in FIG. 17. Rotation knob 58 is molded from a flexible material such as a biocompatible rubber. The proximal end of rotation knob 58 includes a proximal seal 110 having a hole 111 for insertion of endoscope 12 (not shown). The interior of the sheath distal to proximal seal 110 and the interior of ablation cap 82 define an enclosure that is in fluid communication with the interior of the esophagus and the aspiration means of the flexible endoscope 12. Proximal seal 110 prevents fluid communication between the air external to the patient and the interior of sheath 63 and the interior of ablation cap 82. This allows the technique described for FIGS. 18, 19, and 20 for using the suction available with endoscope 12 to pull the interior of the esophagus into intimate contact with electrodes 28 and viewing window 29. Seal 10 also wipes bodily fluids from the exterior of endoscope 12 as it is withdrawn from sheath 63. Rotation knob 58 also includes a distal cylindrical extension 57 that fits tightly over the proximal end of a rotation tube 22 of sheath 63. An external tube 64 fits tightly over the entire length of sheath 63, including the portion attached to distal cylindrical extension 57 of rotation knob 58. Rotation tube 22 may be made of any one of a number of flexible tubing materials, including corrugated polyethylene tubing. External tube 64 is preferably made from polyolefin that is shrink-wrapped tightly onto rotation tube 22 by the application of heat during assembly. In FIG. 21, conductors 18 are shown wrapped around the outside of sheath 63. Conductors 18 may also be assembled between rotation tube 22 and external tube 64 so that the outside of sheath 63 is relatively smooth for passage into the esophagus. Rotation knob 58 also includes a plurality of grip projections to facilitate manipulation.

Figure 22:
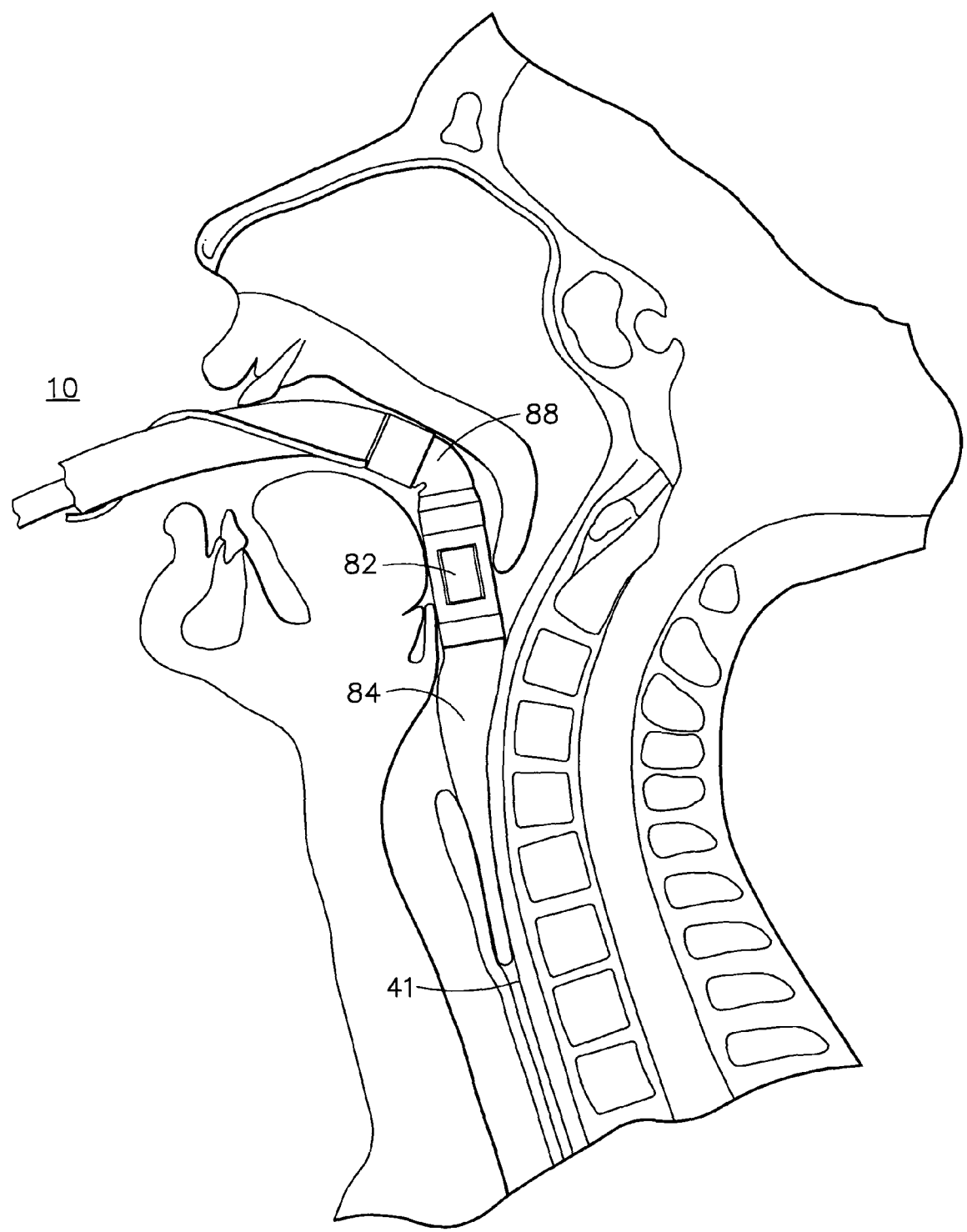
FIG. 22 is a sectional view of the mouth and throat of a patient during intubation of the endoscopic ablation system shown in FIG. 17.

FIG. 22 shows the distal portion of endoscopic ablation system 10 of FIG. 17 partially inserted into the esophagus 41 of a patient. Tapered end cover 84 dilates esophagus 41 as the operator gently inserts ablation cap 82 for positioning near tissue to be ablated. Flexible coupling 88 flexes as shown, reducing the required insertion force and minimizing trauma (and post-procedural pain) to the patient.

Figure 23:
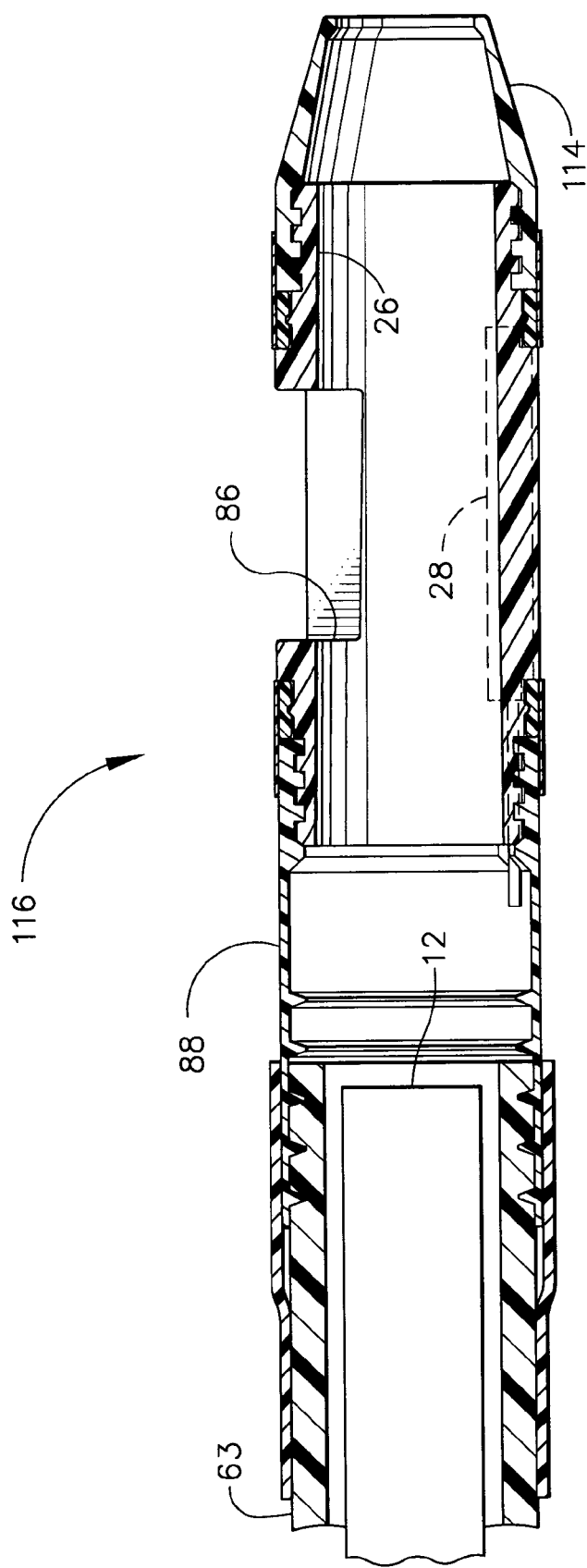
FIG. 23 is a sectional view of the distal portion of a further embodiment of an endoscopic ablation system, which includes an open-end piece 114 (also referred to as a tapered end cover).

FIG. 23 is a sectional view of the distal portion of a further embodiment of an endoscopic ablation system 10. FIG. 23 shows an endoscope 12 inserted into an ablation cap 116 that includes a sheath 63, a plurality of electrodes 28, and a flexible coupling 88 such as was described for FIG. 19. However the embodiment in FIG. 23 includes an open-end piece 114 (also referred to as a tapered end cover) attached to the distal end of rigid support member 26. Open-end piece 114 resembles tapered end cover 84 of FIG. 17, but with all but the proximal portion cut off perpendicular to the longitudinal axis. The remaining taper of open-end piece 114 facilitates passage through the esophagus and substantially prevents body fluids on the esophageal wall from collecting inside ablation cap 116. Open-end piece 114 is made preferably from a flexible material such as silicone rubber. The operator may extend the distal end of endoscope 12 through open-end piece 114, to facilitate endoscopic visualization during intubation of ablation cap 116 into the esophagus. The operator may retract endoscope 12 to a retracted position as shown in FIG. 23 in order to view tissue through a viewing window (not shown) between adjacent electrodes 28, and to watch the progress of ablation.

Now referring again to FIG. 3, the size, shape, and relative position of electrodes 28 are shown, as they would be mounted on rigid support member 26. The region between electrodes 28 forms the viewing window 29. In an endoscopic ablation system according to the present invention, the size, shape and relative position of electrodes 28 are established by the Ablation Index, I, and:

$$I = P/d \quad (1)$$

Where:
P is the perimeter of electrodes 28 and
d is the separation between adjacent edges 8 of electrodes 28.

In the embodiment of the invention illustrated in FIG. 3:

$$I = 2(w+L)/d \quad (2)$$

Where:
w is the width of electrodes 28 and
L is the length of electrodes 28.

Figure 24:
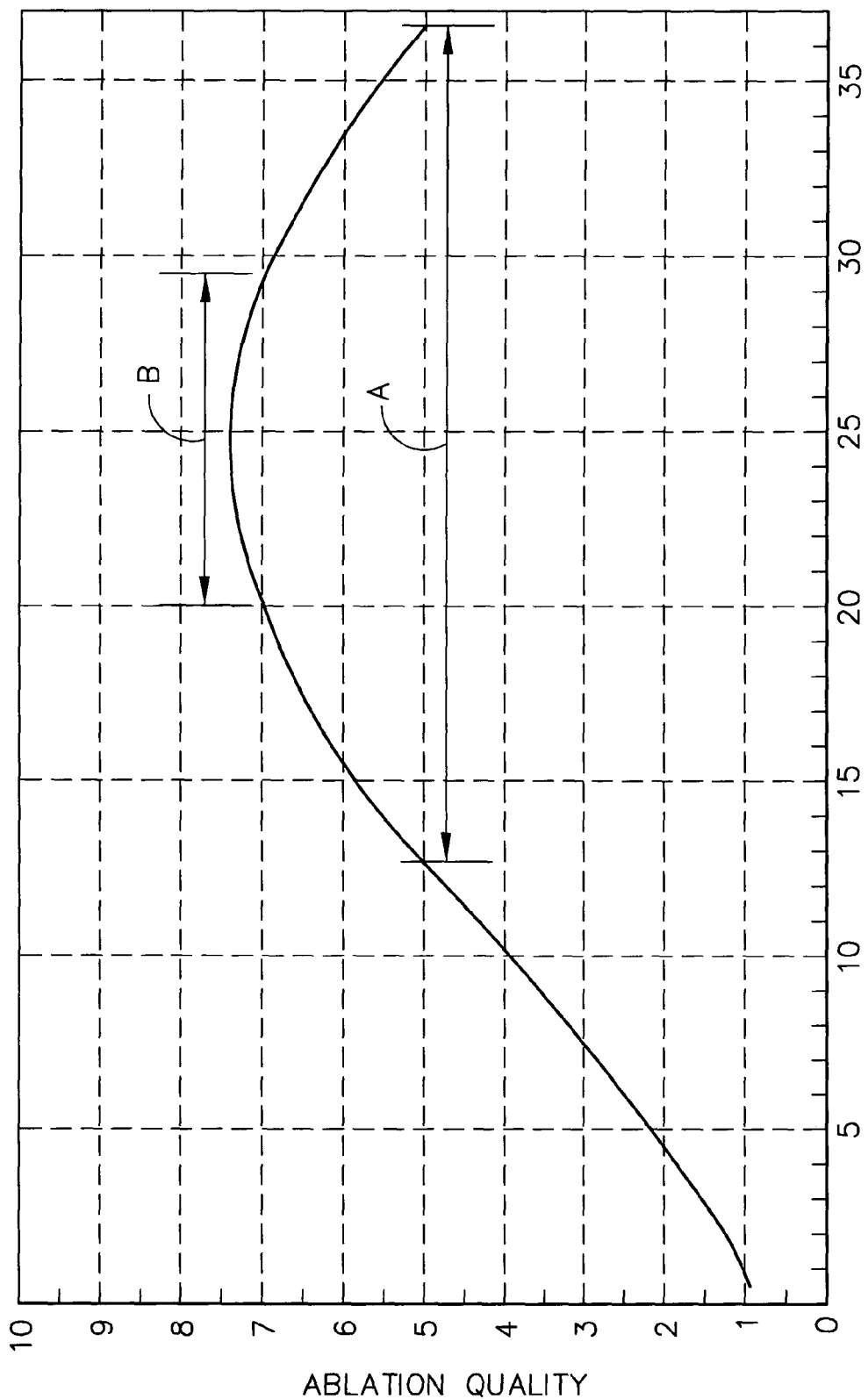
FIG. 24 is a graph showing the relationship of an Ablation Quality to an Ablation Index "I", for the endoscopic ablation system according to the present invention.

Although the electrodes illustrated in FIG. 3 are rectangular in shape, other shapes having an Ablation Index I according to Equation 1 are appropriate for use in the present invention provided that d is substantially constant, i.e. The adjacent edges of the electrodes are substantially parallel. In an endoscopic ablation system according to the present invention, I can be between about 1 and about 200, more particularly between about 15 and 35, such as indicated by a region "A" in the graph of FIG. 24. The graph of FIG. 24 was based on data derived from experiments with many different electrode geometries for many different conditions. Ablation Quality is a subjective rating of between 1–10 based primarily on area, depth, and color of ablation achieved. Region A indicates the Ablation Index I for when Ablation Quality is greater than or equal to 5 (an average subjective rating) on a scale of 1-10. In some cases, the operator may desire to maintain an ablation index where $20 < I < 28$, as indicated by a region "B" in FIG. 24. Practical considerations related to manufacture, type of tissue being treated, physician preferences, and so on, come into play when determining electrode geometry and selecting an ablation index range. The Ablation Index is used to define an electrode arrangement that substantially confines the initial ablation to the tissue under the viewing window, allowing the surgeon to control the ablation process. In operation, an endoscopic ablation device according to the present invention includes electrodes having an Ablation Index within the prescribed ranges. Such an endoscopic ablation instrument will begin to ablate tissue when an electric potential is established between the electrodes (i.e. The electrodes are actuated). However, during the initial ablation process little or none of the tissue directly beneath the electrodes will be ablated and the thermal profile within the treated tissue will have a substantially vertical wall at the edge of the electrodes. Further, the current density of the electrical current flowing between the electrodes will be very high in the tissue under the viewing window, accelerating the ablation of tissue within the treatment region, giving the surgeon precise control of the treatment region and limiting the ablation of healthy tissue. The operator further has precise control of the degree to which the treated tissue is ablated since the operator may view the entire treatment region through the viewing window. The operator may visually determine when the treated tissue is sufficiently ablated by watching to see when the ablated tissue fills the entire ablation window. When the ablated tissue fills the entire ablation window, the mucosa is consistently ablated to a predetermined depth across the treatment region. The actual depth of the ablation is a function of a number of variables, including power. Uniform ablation depths of approximately one to two millimeters are constantly obtainable using the color of the treated tissue in the ablation window as a guide. Ablation depths of one to two millimeters are normally enough to ablate the abnormal tissue in the mucosa without significantly damaging the healthy tissue underneath.

Figure 25:
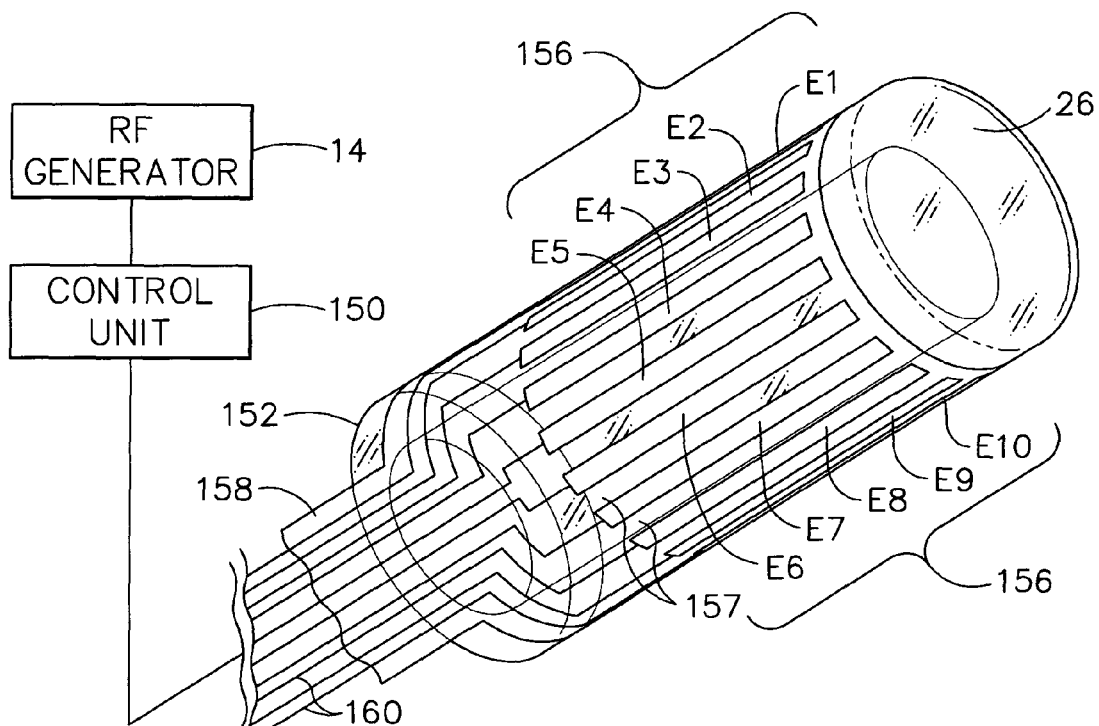
FIG. 25 is an isometric view of ablation cap 20 with a plurality of electrodes 28, which are electrically connected to a control unit 150 and a RF generator.

FIG. 25 represents an endoscopic ablation system 9 comprising an ablation cap 152, a control unit 150, and a RF generator 14. Ablation cap 152 includes a plurality of electrodes 156, each of which is electrically connected to control unit 150. In this embodiment, ten electrodes labeled E1 through E10 comprise plurality of electrodes 156, and are printed using conventional printed circuit manufacturing techniques onto a transparent substrate 158 made from a material such as clear polyacetate or Mylar film. Transparent substrate 158 is adhered to a rigid support member 154 using, for example, UV cured optical adhesive No. NOA 68, which is available from Norland Products, Inc., New Brunswick, N.J. A plurality of electrode leads 160 are also printed onto substrate 158 and terminate at a solder pad (not shown) for electrical attachment to insulated wires (not shown) for electrical connection to control unit 150. Rigid support member 154 may be identical to rigid support member 26 shown in FIG. 2. The proximal end of ablation cap 152 attaches to flexible shaft 32 (see FIG. 1). Electrode leads 160 and portions of electrodes 156 may be covered with a dielectric coating or shrink wrap film in order to be insulated from tissue. In this embodiment, a separate electrode lead is provided for each electrode so that each electrode may be individually actuated by control unit 150 according to a predetermined sequence and for a predetermined duration. This enables a large number of different combinations of electrode actuation sequences and durations to obtain desired tissue ablation effects. It is also possible to have more than one electrode attached to a common lead. Because rigid housing member 154 is made of a clear material such as polycarbonate, a plurality of viewing windows are provided in the spaces between electrodes 156 for endoscopically viewing tissue during the ablation procedure.

Figure 26:
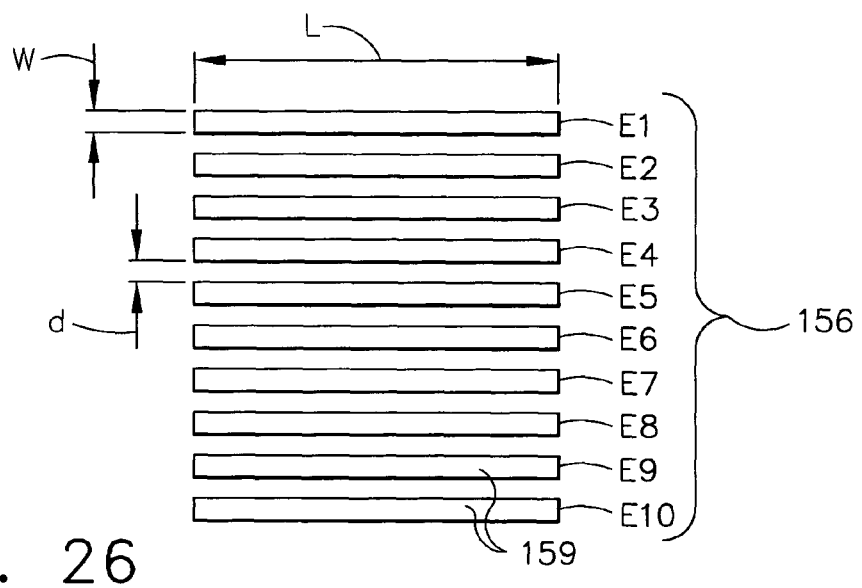
FIG. 26 is a geometric diagram showing the relative size and position of the plurality of electrodes 28 that would be mounted on ablation cap 20 illustrated in FIG. 25.

FIG. 26 shows plurality of electrodes 156 of FIG. 25 as they would appear laid flat. In this embodiment, each of electrodes E1 through E10 has a rectangular shape with length "L" and width "w", and the distance between the parallel edges of adjacent electrodes is "d". As described for FIG. 3, an Ablation Index, I, establishes the size, shape and relative position of electrodes 156 according to the following:

$$I = P/d = 2(w+L)/d \qquad (3)$$

Where:

P is the perimeter of electrodes 156

Although the electrodes illustrated in FIG. 26 are rectangular in shape, other shapes having an Ablation Index, I, according to Equation 3 are appropriate for use in the present invention provided that d is substantially constant. That is, the adjacent edges of the electrodes should be a constant distance apart along the length of the adjacent electrodes. Therefore, it is possible for electrodes 156 to have a curvilinear shape. As described earlier, I can be between about 1 and about 200, more particularly between about 15 and about 35 such as indicated by a region "A" in the graph of FIG. 24. In addition, all of electrodes 156 do not necessarily need to have the same width, length, or distance between electrodes 156. In other embodiments, for example, Ablation Index may vary between pairs of adjacent electrodes to obtain desired tissue ablation effects.

Again referring to FIG. 25, control unit 25 comprises generally an internal switching network for activating plurality of electrodes 156 according to a predetermined sequence and pattern. When any two adjacent electrodes 156 have opposite polarities and are in intimate contact with tissue, the tissue between those two adjacent electrodes is ablated, and tissue underneath the two adjacent electrodes 156 is not ablated. Control unit 25 comprises a programmable, multiplexing system for actuating electrodes 156 and is easily constructable by those skilled in the art. Examples of predetermined sequences of actuation are shown in the following tables where E1–E10 refer to electrodes; T1–T9 refer to time periods, (+) indicates positive polarity, (–) indicates negative polarity, and a blank indicates electrode not energized during the specified time period:

TABLE 1

|    | E1 | E2 | E3 | E4 | E5 | E6 | E7 | E8 | E9 | E10 |
|----|----|----|----|----|----|----|----|----|----|-----|
| T1 | +  | –  |    |    |    |    |    |    |    |     |
| T2 |    | +  | –  |    |    |    |    |    |    |     |
| T3 |    |    | +  | –  |    |    |    |    |    |     |
| T4 |    |    |    | +  | –  |    |    |    |    |     |
| T5 |    |    |    |    | +  | –  |    |    |    |     |
| T6 |    |    |    |    |    | +  | –  |    |    |     |
| T7 |    |    |    |    |    |    | +  | –  |    |     |
| T8 |    |    |    |    |    |    |    | +  | –  |     |
| T9 |    |    |    |    |    |    |    |    | +  | –   |

TABLE 2

|    | E1 | E2 | E3 | E4 | E5 | E6 | E7 | E8 | E9 | E10 |
|----|----|----|----|----|----|----|----|----|----|-----|
| T1 | –  | +  | –  |    |    |    |    |    |    |     |
| T2 |    | –  | +  | –  |    |    |    |    |    |     |
| T3 |    |    | –  | +  | –  |    |    |    |    |     |
| T4 |    |    |    | –  | +  | –  |    |    |    |     |

TABLE 2-continued

| | E1 | E2 | E3 | E4 | E5 | E6 | E7 | E8 | E9 | E10 |
|---|---|---|---|---|---|---|---|---|---|---|
| T5 | | | | | − | + | − | | | |
| T6 | | | | | | − | + | − | | |
| T7 | | | | | | | − | + | − | |
| T8 | | | | | | | | − | + | − |
| T9 | | | | | | | | | − | + |

TABLE 3

| | E1 | E2 | E3 | E4 | E5 | E6 | E7 | E8 | E9 | E10 |
|---|---|---|---|---|---|---|---|---|---|---|
| T1 | − | + | − | | | | | | | |
| T2 | | | − | + | − | | | | | |
| T3 | | | | | − | + | − | | | |
| T4 | | | | | | | − | + | − | |
| T5 | | | | | | | | | − | + |

TABLE 4

| | E1 | E2 | E3 | E4 | E5 | E6 | E7 | E8 | E9 | E10 |
|---|---|---|---|---|---|---|---|---|---|---|
| T1 | − | + | − | + | − | + | − | + | − | + |

In Table 1, electrodes E1 and E2 are energized (on) at time T1, while electrodes E3 through E10 are not energized (off). At time T2, electrodes E2 and E3 are on, while electrodes E1 and E4 through E10 are off, and so on until all tissue in the viewing windows is ablated. The duration of each actuation may vary, but can be approximately 1–2 seconds in one embodiment. By energizing electrodes 156 sequentially in this manner, the peak power requirement for RF generator 14 is significantly less than if all the electrodes 156 were energized simultaneously. Also, while all the electrodes could be energized simultaneously as in Table 4, it may be desirable to energize the electrodes in a sequential manner, as in Tables 1 and 2, so that the tissue ablation can be observed as it occurs through the appropriate window.

A physician may use endoscopic ablation system 9 shown in FIG. 25 in the same manner as was described for endoscopic ablation system 10 of FIGS. 1–5, with one primary difference. That is, the physician will not need to rotate endoscopic ablation system 9 as often within the body lumen as would be required for endoscopic ablation system 10, due to the larger number of electrodes 156 on the former. If the electrodes 156 are disposed around substantially the entire perimeter of the ablation cap, then the device could be rotated within the body lumen only once in either direction, and approximately by a distance equal to the width, w, of an electrode 156, to provide ablation of the tissue around the circumference of the lumen.

In Tables 2 and 3, three electrodes are energized simultaneously. Ten electrodes are shown in FIG. 26, but it will be understood that more electrodes or fewer electrodes could be used, as desired.

FIG. 27 is a sectional view of the distal portion of an endoscopic ablation system 11 including a distally mounted image sensor 120. A flexible endoscope and a conventional video tower are not required for visualization of tissue. Endoscopic ablation system 11 comprises a flexible shaft 138 and a detachable ablation cap 146. Endoscopic ablation system 11 can also be constructed so that ablation cap 146 is not detachable from flexible shaft 138. Flexible shaft 138 includes a sensor housing 140 that contains image sensor 120. Image sensor 120 may be a CMOS (Complementary Metallic Oxide Sensor) camera such as Model Number OV7910,which is available from Omnivision Technologies, Inc. (www.ovt.com). Image sensor 120 may include an objective lens 122 as shown in this embodiment, or may be a pin-hole style CMOS camera that may be used with red light LED illumination, for example. A CMOS cable 124 passing through flexible shaft 138 contains a signal wire for connection to a NTSC or PAL formatted display monitor and a pair of electrical leads for connection to a 5VDC-power supply.

Still referring to FIG. 27, ablation cap 146 comprises a rigid support member 154 made of a clear plastic such as polycarbonate, and may have approximately the same configuration as rigid support member 26 described for FIG. 18. Rigid support element 154 is hollow and has an inner surface 162 and an outer surface 164. A plurality of illuminators 126 are surface mounted on inner surface 162 in order to illuminate the field of view of image sensor 120. White light, surface mounted LED's such as Model No. NSPWF50BS available from Nichia (www.nichia.cojp) are suitable as illuminators 126. Illuminator leads 128 electrically connect in parallel illuminators 126 to a DC power supply (not shown). An umbilical tube 134 has a distal end attached to rigid support member 154 and is long enough to extend outside of the body lumen. Umbilical tube 134 removably attaches to flexible shaft 138 with at least one clip 136. Umbilical tube 134 contains illuminator leads 128, a plurality of bipolar electrode leads 132, and a suction tube 130, which is connected to a vacuum source (not shown).

FIG. 28 is a side view of the distal portion of endoscopic ablation system 11 shown in FIG. 27. In FIG. 28, ablation cap 146 and umbilical tube 134 are shown detached from flexible shaft 138, thus allowing cleaning and reuse of a hermetically sealed and cleanable version of flexible shaft 138 containing image sensor 120. Ablation cap 146 and umbilical tube 134 transport body fluids and support components, especially electrodes 128, that may degrade with repeated use, and therefore may be fabricated as single patient use, disposable components. FIG. 28 shows one of many variations of attaching ablation cap 146 to flexible shaft 138. Each of at least one retaining slots 144 engages with a corresponding post 142 projecting radially from a boss 141 on the distal end of flexible shaft 138. (This variation of attaching two components is commonly referred to as a "bayonet fitting.")

Figure 29:
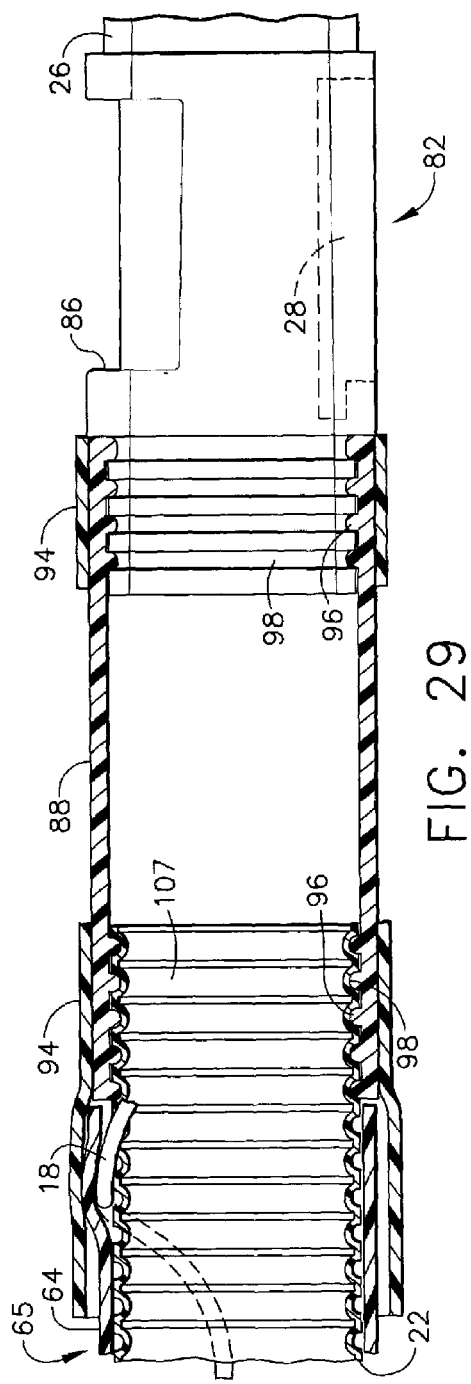
FIG. 29 is a cross sectional illustration of the distal end of a medical device including a laminate elongate hollow member according to one embodiment of the present invention.
Figure 30:
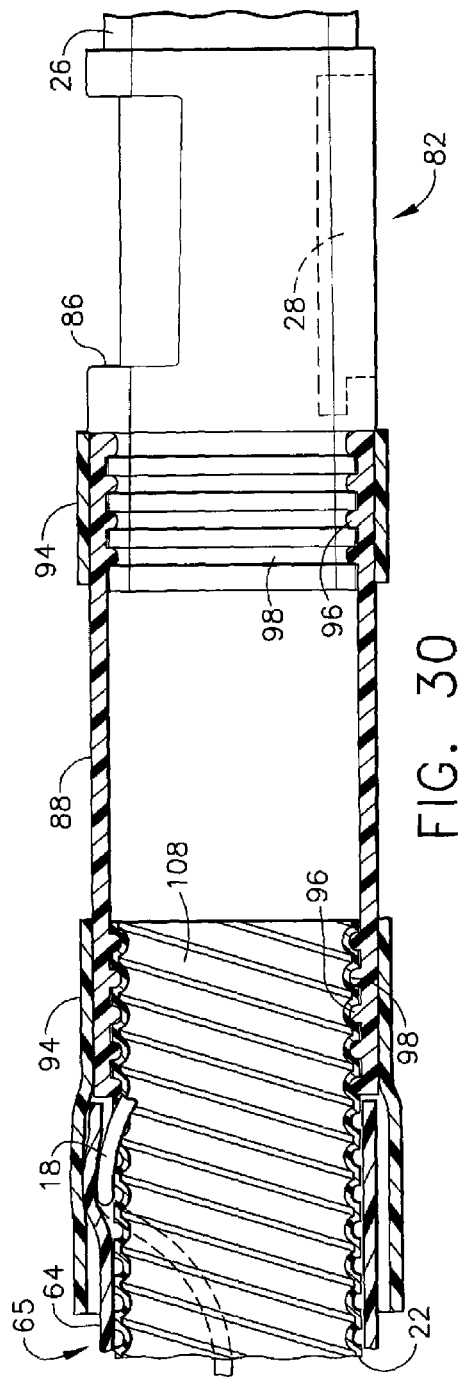
FIG. 30 is a cross sectional illustration of the distal end of a medical device including a laminate elongate hollow member according to another embodiment of the present invention.

FIGS. 29 and 30 show embodiments of a medical device according to the present invention comprising a laminate wall construction. In FIG. 29, an ablation device is shown having a laminate elongated hollow member, such as a laminate sheath 65. The laminate elongated hollow member can comprise a corrugated rotation tube 22. Electrical conducters 18 for providing electrical energy to electrodes 28 are shown disposed intermediate the corrugated rotation tube 22 and an outer layer, such as an external tube 64, which is disposed radially outward of the corrugated rotation tube 22. External tube 64 can comprise a shrink wrap material, and can be employed to secure conductors 18 closely against the outer surface of rotation tube 22, or within grooves or other surface features on the outside surface of rotation tube 22.

Rotation tube 22 provides a lumen for receiving endoscope 12, and supplies torsional rigidity to ablation system 10 so that rotation by the operator at the proximal end results in substantially the same rotation at the distal end. The corrugations of tube 22 can also provide bending flexibility so that the medical device can be comfortably inserted into the patient's esophagus. By "corrugated" it is meant that tube 22 comprises an alternating pattern of raised and depressed surface features, such as ridge and groove features, which features may be arranged in parallel along the length of rotation tube 22 (e.g. such as parallel raised rings postioned along the length of the tube), or which features may be arranged in a spiral fashion (such as in the fashion of screw threads or otherwise convoluted) along the length of the tube. Such a corrugated construction can provide sufficient torsional stiffness in combination with sufficient bending flexibility for insertion into a patient. FIG. 29 shows an embodiment in which rotation tube 22 comprises corrugated tubing 107 having raised and depressed surface features which are spaced in a parallel fashion along the length of the tubing 107. FIG. 30 shows an embodiment in which rotation tube 22 comprises corrugated tubing 108 in which the surface features of tubing 108 (e.g. one or more groove) are arranged in a spiral fashion along the length of tubing 108.

If desired, a third layer can be included, such as for instance a thin, smooth tube or wrap material can be disposed coaxially within the rotation tube 22 to cover the surface features on the internal diameter of rotation tube 22. Alternatively, a foam or other suitable material can be provided to fill the internal surface features of rotation tube 22 so that rotation tube 22 has a generally smooth internal surface. In yet another embodiment, rotation tube 22 may be provided with a smooth internal surface and an outer surface having surface features such as grooves and ridges.

Rotation tube 22 may be made from numerous plastic materials including, but not limited to, polyethylene, FEP (Fluorinated Ethylene Propylene), or PTFE (Polytetrafluoroethylene). In the embodiment shown, the distal portion of rotation tube 22 may attach to the proximal portion of flexible coupling 88, wherein spaced, radially inward facing projections 96 on the interior surface of coupling 88 engage one or more grooves 98 in the outer surface of rotation tube 22. Similarly, groove 98 and projection 96 surface features can be employed to connect coupling 88 to rigid support member 26. Rings 94 (which may provide a radially inward biasing force on coupling 88) may be used on both the proximal and distal ends of coupling 88 to secure the flexible coupling 88 to the rotation tube 22 and the support member 26.

The sheath 65 can have a wall thickness which is at least about 0.090 inch, and more particularly at least about 0.100 inch. In one embodiment, the inner diameter of the rotation tube 22 is about 11 mm, and the outer diameter measured at the outer surface of the outer tube 64 can be about 16 mm to about 18 mm, and the resulting wall thickness of the sheath 65 can be between about 2.5 mm (0.098 inch) and about 3.5 mm (0.138 inch).

Figure 31:
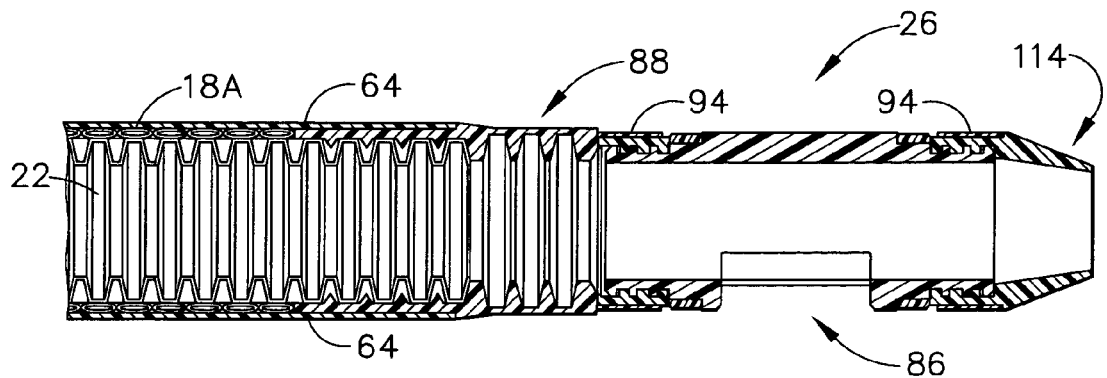
FIG. 31 provides a cross sectional illustration of the distal end of a medical device including a laminate elongate hollow member according to another emobidment of the present invention.
Figure 32:
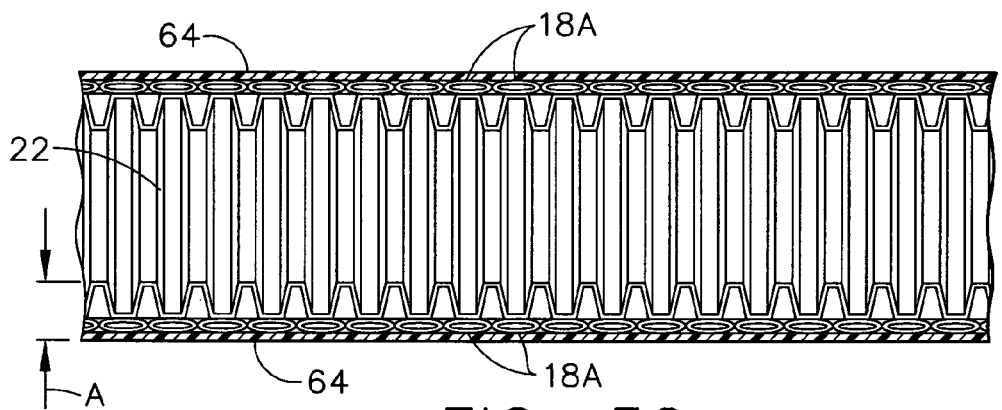
FIG. 32 provides an enlarged cross sectional illustration of a portion of the device of FIG. 31 showing electrical conductors in the form of ribbon cable disposed between an inner corrugated tube and an outer layer.

FIG. 31 illustrates another embodiment of an ablation device according to the present invention comprising, among other features, a modified flexible coupling 88 and conductors in the form of ribbon cable 18A, which can comprise a plurality of electrical conductors separated by insulation. Ribbon cable 18A can be relatively flat for providing a thin profile, and can be spiral wound about rotation tube 22, and can be disposed between rotation tube 22 and an outer layer 64 of heat shrink material, as shown in FIG. 32. Suitable ribbon cable 18A is available as Ribbon Cable #9L28025, 25 conductor, 28AWG from Belden Cable Co. Ribbon cable 18A carries electrical energy to the electrodes on support member 26, and can also be used to carry other control or energy signals.

In FIG. 31 rotation tube 22 comprises polyethylene corrugated tubing and can have a gauge of about 0.005 inch, such as is available from New Age Industries of Southampton, Pa., as part number 2570341, with an inner diameter of between about 0.405 inch and about 0.437 inch, and an outer diameter of between about 0.573 inch and about 0.594 inch. Referring to FIG. 32, the wall thickness A of the laminate of the tube 22, ribbon cable 18A, and heat shrink outer layer 64 can be between about 0.120 inch and about 0.154 inch.

Figure 33:
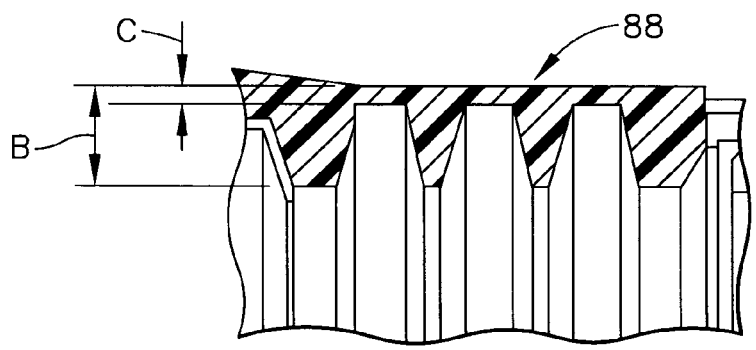
FIG. 33 provides an enlarged cross sectional illustration of a portion of a flexible coupling illustrated in FIG. 32.

Referring to FIGS. 31 and 33, the modified flexible coupling 88 is disposed between the rotation tube 22 and the support member 26, and has a corrugated inner surface. The flexible coupling can be formed of any suitable flexible material, including synthetic materials and rubber materials. In one embodiment, the flexible coupling can be formed of silicone rubber. Referring to FIG. 33, the flexible coupling can have a wall thickness B of about 0.105 to about 0.115 inch, and a local material dimension C of about 0.020 inch.

The support member 26 can be formed of a generally transparent polycarbonate material. Distal tip 114 can comprise a flexible silicone rubber member which has a generally frustoconical shape, and can be sized and shaped to resiliently deform inwardly when vacuum is applied through rotation tube 22. Accordingly, distal tip 114 can provide sealing at the distal end of the medical device when vacuum is applied through tube 22, while providing an opening through which an endoscope or other instrument may pass.

The devices shown in the figures may be used in or with other surgical instruments such as, for example, endocutters. Further, the devices may be used for other treatment regimens such as tissue welding, electrophoresis and coagulation of varicose veins and hemorrhoids. While preferred embodiments of the present invention have been shown and described herein, it will be obvious to those skilled in the art that such embodiments are provided by way of example only. Numerous variations, changes, and substitutions will now occur to those skilled in the art without departing from the invention. Further, the particular structural features disclosed and used to perform a particular function can be alternatively referred to and described in terms of a means for performing the structure's function. Accordingly, it is intended that only the spirit and scope of the appended claims limit the invention.

What is claimed is:

1. A medical device adapted for insertion into a body lumen, the medical device comprising; a relatively flexible corrugated tube; a relatively rigid support member disposed distally of the corrugated tube, wherein the support member comprises a side opening for providing access to tissue, and wherein the side opening is spaced proximally from a distal end of the support member and wherein the side opening extends through an outer surface of the support member; a flexible coupling disposed intermediate the relatively rigid support member and the relatively flexible corrugated tube; and at least two electrodes supported on the outside surface of the relatively rigid support member, and wherein a portion of the rigid support member disposed between the two electrodes is generally transparent.

2. The medical device of claim 1 wherein each of the corrugated tube, die flexible coupling, and the support member include an internal passageway sized to receive an endoscope.

3. The device of claim 1 wherein the corrugated tube has an internal passageway sized to receive an endoscope.

4. The device of claim 1 further comprising a layer disposed radially outwardly of the corrugated tube.

5. The device of claim 4 comprising at least one electrical conductor disposed intermediate the corrugated tube and the layer disposed radially outwardly of the corrugated tube.

* * * * *